(12) United States Patent
Araoz et al.

(10) Patent No.: US 10,073,089 B2
(45) Date of Patent: Sep. 11, 2018

(54) METHOD FOR MANUFACTURING AN ANALYSIS SUBSTRATE, AND USE THEREOF FOR DETECTING TOXINS

(75) Inventors: Romulo Araoz, Gif-sur-Yvette (FR); Hoang-Oanh Nghiem, Paris (FR); Jordi Molgo, Antony (FR); Luis Botana, Lugo (ES); Natalia Vilarino, Lugo (ES)

(73) Assignee: ABRAXIS LLC, Warminster, PA (US)

( * ) Notice: Subject to any disclaimer, the term of this patent is extended or adjusted under 35 U.S.C. 154(b) by 29 days.

(21) Appl. No.: 13/981,859

(22) PCT Filed: Jan. 24, 2012

(86) PCT No.: PCT/FR2012/050157
§ 371 (c)(1),
(2), (4) Date: Jul. 25, 2013

(87) PCT Pub. No.: WO2012/101378
PCT Pub. Date: Aug. 2, 2012

(65) Prior Publication Data
US 2013/0303405 A1 Nov. 14, 2013

(30) Foreign Application Priority Data
Jan. 25, 2011 (FR) ...................................... 11 50586

(51) Int. Cl.
| | | |
|---|---|---|
| *G01N 33/543* | (2006.01) | |
| *G01N 33/567* | (2006.01) | |
| *C40B 40/10* | (2006.01) | |
| *G01N 33/50* | (2006.01) | |
| *G01N 33/53* | (2006.01) | |
| *G01N 33/554* | (2006.01) | |

(52) U.S. Cl.
CPC ........ *G01N 33/543* (2013.01); *G01N 33/5014* (2013.01); *G01N 33/54366* (2013.01); *G01N 33/554* (2013.01); *G01N 33/567* (2013.01); *C40B 40/10* (2013.01); *G01N 2333/4603* (2013.01); *G01N 2333/70571* (2013.01)

(58) Field of Classification Search
CPC .... G01N 33/543; G01N 33/53; G01N 33/569; G01N 33/5014; G01N 33/54366; C40B 40/10
USPC ..................... 506/18; 435/7.2, 7.92
See application file for complete search history.

(56) References Cited

U.S. PATENT DOCUMENTS

| | | | | |
|---|---|---|---|---|
| 6,040,191 A | * | 3/2000 | Grow ............................. | 506/12 |
| 2002/0094544 A1 | * | 7/2002 | Fang et al. .................... | 435/7.9 |
| 2004/0002064 A1 | * | 1/2004 | Fang et al. ....................... | 435/5 |

FOREIGN PATENT DOCUMENTS

| | | |
|---|---|---|
| EP | 1376124 A2 | 1/2004 |
| WO | WO 2009138519 A1 * 11/2009 | ......... C07K 16/2866 |

OTHER PUBLICATIONS

Hill et al., "Serine-Specific Phosphorylation of Nicotinic Receptor Associated 43K Protein," Biochemistry 1991, 30:5579-5585.*
Sullivan et al., "Assay Development in High Density MicroWell Plates: Use of Well Geometries, Format, Surface Modification and Optical Properties to Achieve Optimal Assay Performance," Journal of the Association for Laboratory Automation 2001, 6(2):47-52.*
Romulo Araoz et al. "Ligand-binding assays for cyanobacterial neurotoxins targeting cholinergic receptors", Analytical and Bioanalytical Chemistry, Mar. 19, 2010, pp. 1618-2650, vol. 397, No. 5, Berlin Germany.
Romulo Araoz et al. "A non-radioactive ligand-binding assay for detection of cyanobacterial anatoxins using Torpedo electrocyte membranes", Toxicon, Jul. 1, 2008, pp. 163-174, vol. 52, No. 1, New York.
Eva S. Fonfria et al. "Detection of 13,19-didesmethyl C spirolide by flourescence polarization using Torpedo electrocyte membranes", Analytical Biochemistry, Aug. 1, 2010, pp. 102-107, vol. 403, No. 1-2, Academic Press Inc. New York.
International Search Report dated Apr. 5, 2012, re: PCT/FR2012/050157.
Natalia Vilarino et al. "Detection of Gymnodimine-A and 13-Desmethyl C Spirolide Phycotoxins by Fluorescence Polarization", Analytical Chemistry, Apr. 1, 2009, pp. 2708-2714, vol. 81, No. 7.
Zouher Amzil et al. "Report on the First Detection of Pectenotoxin-2, Spirolide-A and Their Derivatives in French Shellfish"; Marine Drugs; 2007; vol. 5; pp. 168-179; www.mdpi.org/marinedrugs.
Romulo Araoz et al. "Neurotoxic Cyanobacterial Toxins"; Toxicon; 2010; vol. 56; pp. 813-828; www.elsevier.com/locate/toxicon.
Yves Bourne et al. "Structural determinants in phycotoxins and AChBP conferring high affinity binding and nicotinic AChR antagonism"; Proc. Natl. Acad. Sci.; vol. 107; No. 13; pp. 6076-6081.
Sabrina Cadel-Six et al. "Different Genotypes of Anatoxin-Producing Cyanobacteria Coexist in the Tarn River, France"; Applied and Environment Microbiology; Dec. 2007; vol. 73; No. 23; pp. 7605-7614.

(Continued)

*Primary Examiner* — Kaijiang Zhang
(74) *Attorney, Agent, or Firm* — Cantor Colburn LLP

(57) ABSTRACT

The présent invention relates to a method for manufacturing an analysis device including torpédo membrane fragments immobilized at the surface thereof, to the resulting analysis device, and to the use of said device for detecting, purifying, and characterizing molécules acting on nicotinic acetylcholine receptors. The présent invention is useful in the field of monitoring seafood, monitoring neurotoxic phytoplankton for the shellfish industry, monitoring the quality of bathing waters along tourist beaches, the field of monitoring fresh water reserves, the field of médical research, the field of the biological analysis and characterization of molécules, e.g., non-radioactive assays of the movement of the ligand-receptor bond on an ELISA-type microplate, thereby enabling compétitive agonists and antagonists of targets to be detected, e.g., of highly sensitive receptors.

24 Claims, 7 Drawing Sheets

(56) References Cited

OTHER PUBLICATIONS

Jean-Pierre Changeux "Allosteric Receptors: From Electric Organ to Cognition"; Annual Review of Pharmacology and Toxicology; 2010; vol. 50; pp. 1-38. www.pharmtox.annualreviews.org.
Cloture des Assises de la conchyliculture (Oct. 15, 2010). Discours de Bruno Le Maire, Ministre de l'Alimentation, de l'Agriculture et de la Peche) (http://agriculture.gouv.fr/cloture-des-assises-de-la).
Corrie J. B. Dacosta et al. "Role of Glycosylation and Membrane Environment in Nicotinic Acetylcholine Receptor Stability"; Biophysical Journal; Mar. 2005; vol. 88; pp. 1755-1764.
Directive 2010/63/UE du Parlement européen et du Conseil du Sep. 22, 2010 relative à la protection des animaux utilisés à des fins scientifiques. Journal officiel de l'Union européenne. Douefr, Oct. 20, 2010 (http://eu.vlex.com/source/journal-officiel-union-europeenne-1547/issue/2010/10/20/01).
Peter Esser "Principles in Adsorption to Polystyrene"; Technical Bulletin: 06a; Thermo Fisher Scientific, Inc.; 6 pages.
L.E. Fleming et al. "Oceans and human health: Emerging public health risks in the marine environment", Science Direct; Marine Pollution Bulletin: 2006; vol. 53; pp. 545-560; www.sciencedirect.com.
Muriel Gugger et al. "First report in a river in France of the benthic cyanobacterium Phormidium favosum producing anatoxin-a associated with dog neurotoxicosis"; Toxicon; 2005; vol. 45; pp. 919-928.

Joseph A. Hill et la. "Serine-Specific Phosphorylation of Nicotinic Receptor Associated 43K Protein"; Biochemistry; American Chemical Society; 1991; vol. 30; pp. 5579-5585.
Riadh Kharrat et al. "The marine phycotoxin gymnodimine targets muscular and neuronal nicotinic acetylcholine receptor subtypes with high affinity", Journal of Neurochemistry; 2008; vol. 107; pp. 952-963.
Jordi Molgo et al. "Cyclic Imines: An Insight into this Emerging Group of Bioactive Marine Toxins"; In Phycotoxins: Chemistry and Biochemistry; 2007; pp. 319-335.
N. Morel et al. "Large-scale Purfiication of Presynaptic Plasma Membranes from Torpedo marmorata Electric Organ"; The Journal of Cell Biology; Nov. 1985; vol. 101; pp. 1757-1762.
Romulo Araoz et al. "Total Synthesis of Pinnatoxins A and G and Revision of the Mode of Action of Pinnatoxin A"; NIH Public Access; J Am Chem Soc.; Jul. 13, 2011; vol. 27; pp. 10499-10511.
Kaarina Sivonen et al. "Toxic Cyanobacteria in Water: A guide to their public health consequences, monitoring and management"; WHO; 1999; pp. 41-111.
Araoz et al.; "Coupling the Torpedo Microplate-Receptor Binding Assay with Mass Spectrometry to Detect Cyclic Imine Neurotoxins"; American Chemical Society, vol. 84; 2012; pp. 10445-10453.
Mate et al.; "Integrated genomics and proteomics of the Torpedo caiifornica electric organ: concordance with the mammalian neuromuscular junction"; Skeletal Muscle, vol. 1; No. 20; 2011; pp. 1-17.

* cited by examiner

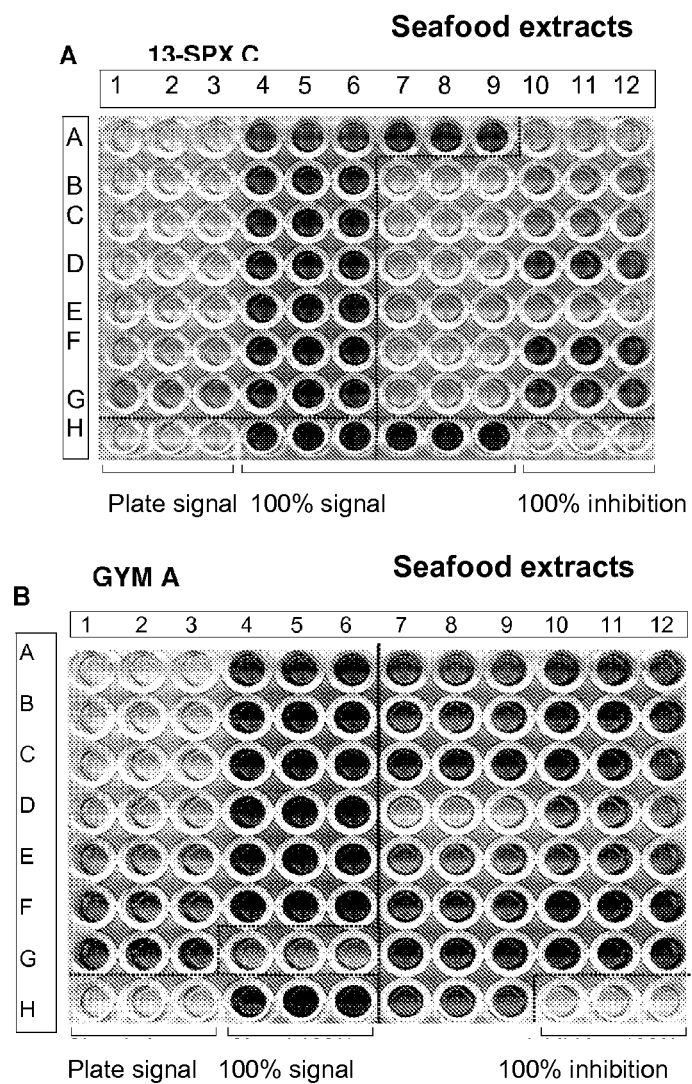
FIGURE 4 (1/2)

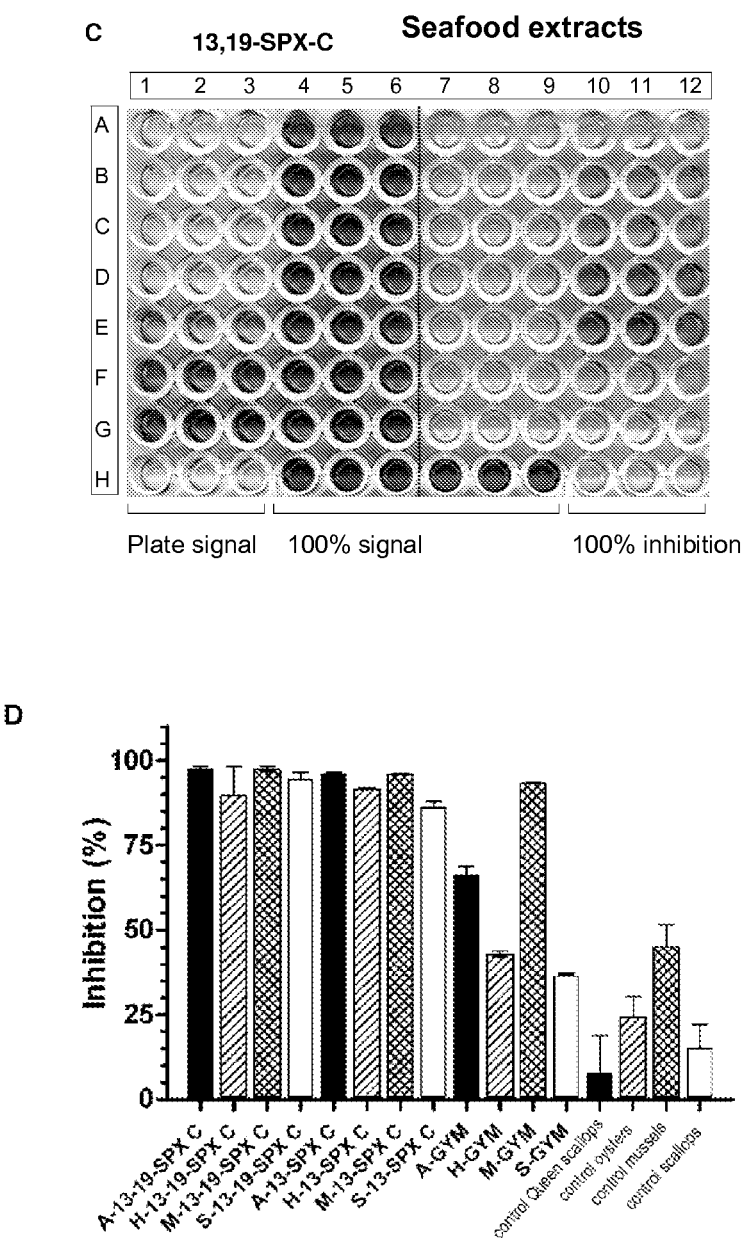
FIGURE 4 (2/2)

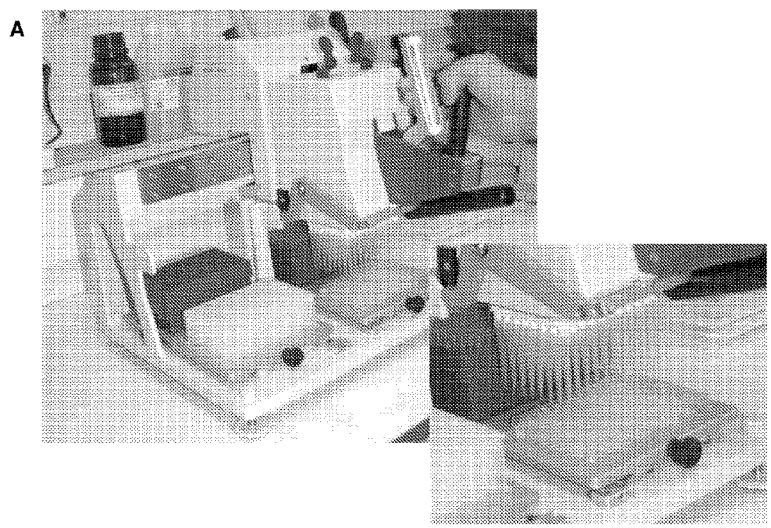
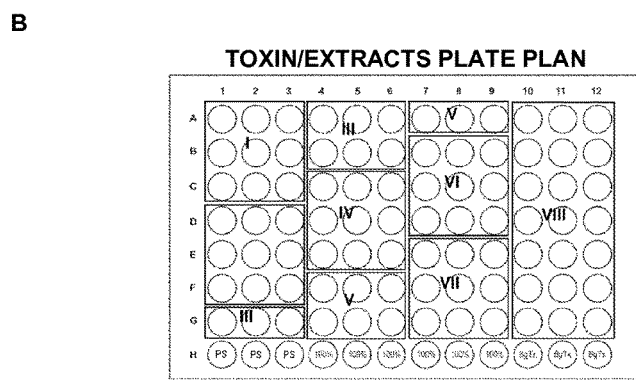
FIGURE 5 (1/2)

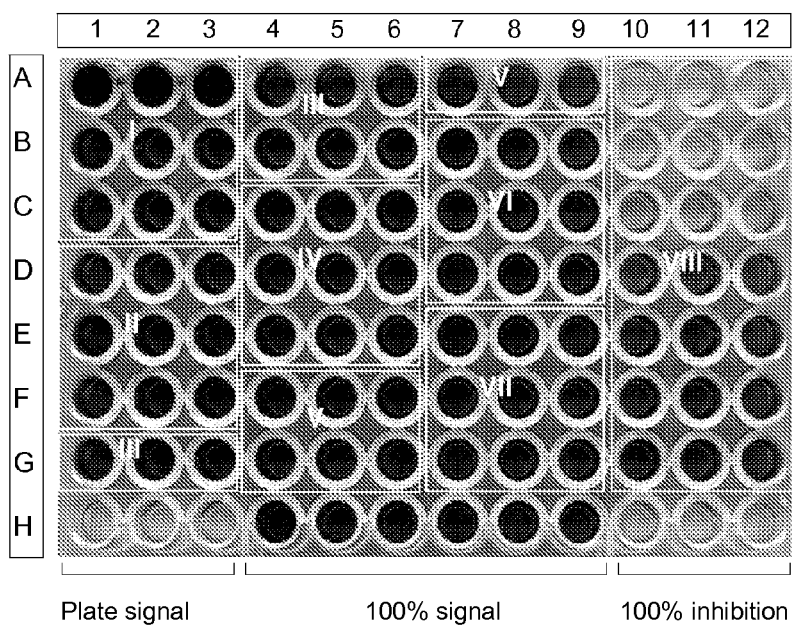
FIGURE 5 (2/2)

METHOD FOR MANUFACTURING AN ANALYSIS SUBSTRATE, AND USE THEREOF FOR DETECTING TOXINS

TECHNICAL FIELD

The present invention relates to a method for manufacturing an analysis device comprising torpedo membrane fragments immobilized at the surface thereof, to the analysis device obtained and to the use of said device for detecting and characterizing molecules, in particular competitive ligands of nicotinic acetylcholine receptors.

The present invention is in particular of use in the field of monitoring seafood, in the field of monitoring freshwater reserves, in the field of medical research, and in the field of the biological analysis and characterization of molecules.

In the description below, the reference between square brackets ([ ]) refer to the list of references given at the end of the text.

PRIOR ART

According to recent European directives, Directive 2010/63/EU [1], the "mouse test", which was the only official test used for monitoring marine toxins, must be replaced with prevalidated functional methods. Particularly in France, the "mouse test" was replaced with physicochemical methods for seafood health monitoring starting from 2010 (Closure of the Shellfish Farming Conference (Oct. 15, 2010). Speech by Bruno Le Maire, minister of food, agriculture and fisheries) (http://agriculture.gouv.fr/cloture-des-assises-de-la) [2].

Effluorescences of marine dinoflagellates, when they are dominated by a toxic species, represent a danger to the marine ecosystem, commercial activities and public health. This is because the phycotoxins of dinoflagellates can be accumulated by molluscs and fish and, via vectorial transport, can reach humans (Fleming L E, Broad K, Clément A, Dewailly E, Elmir S, Knap A, Pomponi S A, Smith S, Gabriele H S, Walsh P (2006) Oceans and human health: Emerging public health risks in the marine environment. Mar. Pollut. Bull., 53: 545-560 [3], Molgô J, Girard E, Benoit E. (2007) Cyclic imines: an insight into this emerging group of bioactive marine toxins. In *Phycotoxins: Chemistry and Biochemistry* (Botana, L. M., ed) pp. 319-335, Blackwell Publishing Ltd, Iowa [4]). In 2005, the Phytoplankton Monitoring Network detected, by means of the "mouse test", molluscs contaminated with unknown neurotoxins in samples from the Arcachon basin. Consequently, the French state decreed that it was prohibited to consume oysters and shellfish from the Arcachon basin and had to release 2.5 million Euros in aid for the shellfish industry of the Region of Arcachon, France. Later on, spirolide A and 13-desmethyl spirolide-C, which are toxins produced by the dinoflagellate *Alexandrium ostenfeldii*, were detected in oysters and mussels from the Arcachon basin (Amzil Z, Sibat M, Royer F, Masson N, Abadie E. (2007) Report on the first detection of pectenotoxin-2, spirolide-A and their derivatives in French shellfish. Mar. Drugs 5: 168-179) [5].

In the context of the ANR Neurospiroimine program (research program financed by the National Research Agency (ANR) (PCV07-1 9441 7-Neurospiroimine)), the mechanism of action of cyclic imines of the spirolide and gymnodimine family was established (Bourne Y, Radic Z, Araôz R, Talley T T, Benoit E, Servent D, Taylor P, Molgô J, Marchot P. (2010) Structural determinants in phycotoxins and AChBP conferring high affinity binding and nicotinic AChR antagonism. Proc. Natl. Acad. Sci. U.S.A. 107: 6076-6081 [6]). Neurotoxins of the spirolide, gymnodimine and pinnatoxin family are powerful muscle- and neuronal-type nicotinic acetylcholine receptor (nAChR) antagonists which have affinities in the picomolar and nanomolar order (Bourne Y, Radie Z, Araôz R, Talley T T, Benoit E, Servent D, Taylor P, Molgô J, Marchot P. (2010) Structural determinants in phycotoxins and AChBP conferring high affinity binding and nicotinic AChR antagonism. Proc. Natl. Acad. Sci. U.S.A. 107: 6076-6081 [6]), Kharrat R, Servent D, Girard E, Ouanounou G, Amar M, Marrouchi R, Benoit E, Molgô J. (2008) The marine phycotoxin gymnodimine targets muscular and neuronal nicotinic acetylcholine receptor subtypes with high affinity. J. Neurochem. 107, 952-963 [7], Araôz R, Servent D, Molgô J, Iorga B I, Fruchart-Gaillard C, Benoit E, Gu Z, Stivala C, Zakarian A (2011) Total synthesis of pinnatoxins A and G and revision of the mode of action of pinnatoxin A. J. Am. Chem. Soc. 133, 10499-10511 [8]).

The current methods for detecting toxins in the shellfish industry, i.e. marine phycotoxins, are mainly:

the "mouse test" which must, by virtue of the change in European regulations, be replaced with a test which does not use animals. Currently in France, the "mouse test" is only used in the context of shellfish health monitoring (Closure of the Conference on shellfish farming (Oct. 15, 2010). Speech by Bruno Le Maire, minister of food, agriculture and fisheries) (http://agriculture.gouv.fr/cloture-des-assises-de-la) [2]). Furthermore, this test is difficult to carry out and requires considerable infrastructures (i.e. animal house) for its implementation. In addition, those working in shellfish farming question the validity of this test and contest the results obtained;

high performance liquid chromatography (HPLC). This method is expensive, requiring considerable equipment which is expensive and not very sensitive;

HPLC coupled to mass spectrometry (LC-MS). This method is expensive, requiring considerable equipment which is expensive and qualified personnel in order to use said equipment. Despite its high sensitivity and specificity, this method requires standard toxins in order to calibrate the equipment for their detection. In addition, the LC-MS method has limited use in the context of the detection of unknown toxins. Since 2010, LC-MS has been the official method for detecting or monitoring marine phycotoxins which are subject to regulation in France, thus relegating the mouse test to the role of seafood health monitoring (Closure of the Conference on shellfish farming (Oct. 15, 2010). Speech by Bruno Le Maire, minister of food, agriculture and fisheries) (http://agriculture.gouv.fr/cloture-des-assises-de-la) [2]). However, the LC-MS method does not make it possible to and cannot be used to detect new toxins.

There is therefore a real need to find a method and/or a device which is simple and inexpensive, for example a functional test for detecting toxins, in particular neurotoxins, for example phycotoxins of the cyclized imine family, for example the gymnodimine, spirolide, pinnatoxin, pteriatoxin, prorocentrolide and spiro-prorocentrimine family, or new toxins, for example pinnamine, acting on nAChRs, for example for monitoring neurotoxic phytoplankton for the shellfish industry or the quality of bathing water along tourist beaches, and also for monitoring contaminated seafood.

Similarly, the proliferation of cyanobacteria in freshwater reserves constitutes a potential danger to public health. This is because cyanobacterial species can produce neurotoxins; they may, for example, be toxic species of the *Anabaena* or *Oscillatoria* genus or others producing anatoxin-a or homoanatoxin-a (Sivonen K, Jones G. (1999) Cyanobacterial toxins. *In Toxic cyanobacteria in water: a guide to their public health consequences, monitoring and management* (Chorus I., ed) pp. 41-111, Bartram, J. E. & F. N. Spon, London [9]). Admittedly, numerous episodes of poisoning of dogs having drunk water with a high content of cyanobacteria producing anatoxin-a and homoanatoxin-a, which are powerful nAChR antagonists, have occurred in France in rivers such as the Loue (2003) and the Tarn (2002, 2003 and 2005) (Gugger M, Lenoir S, Berger C, Ledreux A, Druart J C, Humbert J F, Guette C, Bernard C. (2005) First report in a river in France of the benthic cyanobacterium *Phormidium favosum* producing anatoxin-a associated with dog neurotoxicosis. Toxicon 45, 919-928 [10], Cadel-Six S, Peyraud-Thomas C, Brient L, Tandeau de Marsac N, Rippka R, Mejean A. (2007) Different genotypes of anatoxin-producing cyanobacteria coexist in the Tarn River, France. Applied and Environmental Microbiology 73, 7605-7614. [11]).

The current methods for detecting cyanobacterial neurotoxins are mainly:

HPLC: this method is expensive, requiring considerable equipment which is expensive and not very sensitive.

HPLC coupled to mass spectrometry (LC-MS). This method is expensive and requires considerable equipment which is expensive, and also qualified personnel in order to use this equipment.

There are also in the prior art methods for the detection in solution of compounds such as 13,19-didesmethyl spirolide C, gymnodimine A and 13-desmethyl spirolide C (Fonfria et al. "Detection of 13,19-didesmethyl spirolide C by fluorescence polarization using torpedo electrocyte membranes" Analytical Biochemistry, Vol 403: 1-2, 2010, p 102-107 [12], Vilariho et al. "Detection of gymnodimine-A and 13-desmethyl spirolide C phycotoxins by fluorescence polarization", Analytical Chemistry, Vol 81: 7, p 2708-2714 [13]) or of cyanobacterial anatoxin-a and homoanatoxin-a (Aràoz et al. "A non radioactive ligand-binding assay for detection of cyanobacterial anatoxins using torpedo electrocyte membranes", Toxicon, Vol 52:1, p 163-174 [14]). However, these methods have low detection sensitivities and require for the detection of said compounds the use of considerable equipment, such as polarization fluorometers, and chemiluminescence detectors which are expensive and complex, thus requiring qualified personnel for their implementation and use.

There is therefore a real need to find a method and/or a device, in particular a device which is simple and inexpensive, for example a functional test, for identifying cyanobacterial toxins acting on nAChRs, for example for controlling the quality of freshwater reserves, the monitoring of cyanobacterium-based food supplements, and the quality of bathing water, making it possible to reduce costs and the processing time, and to improve the reliability of the results obtained.

DESCRIPTION OF THE INVENTION

The present invention makes it possible to solve and to overcome the abovementioned obstacles and drawbacks of the prior art by providing a method for manufacturing an analysis device comprising *Torpedo* membrane fragments immobilized at the surface thereof, comprising the steps of:

a. isolating *Torpedo* electrocyte cell membranes,
b. fragmenting said isolated membranes,
c. incorporating the membrane fragments obtained in step b) into a solution with a pH between from 6.5 to 10,
d. attaching said membrane fragments to the surface of the device.

According to the invention, the term "electrocyte cells" is intended to mean modified muscle cells having lost their ability to contract and which are specialized in generating electricity. The electrocytes may be derived from the electric organ of electric fish, for example of the species of the Torpedinidae family, such as *Torpedoes*, or of the family Electrophoridae, such as the electric eel (*Electrophorus electricus*).

According to the invention, the cells may be cells derived from the *Torpedo* electric organ, for example, electrocytes of *Torpedoes* chosen from the group comprising *Torpedo adenensis*, *Torpedo alexandrinsis* or Alexandrine torpedo, *Torpedo andersoni* or Florida torpedo, *Torpedo bauchotae*, *Torpedo californica* or Pacific electric ray, *Torpedo fairchildi*, *Torpedo fuscomaculata*, *Torpedo mackayana*, *Torpedo macneilli*, *Torpedo marmorata*, or marbled electric ray or marbled *Torpedo* ray, *Torpedo microdiscus*, *Torpedo nobiliana* or Atlantic electric ray, *Torpedo panthera* or Panther torpedo ray, *Torpedo peruana*, *Torpedo semipelagica*, *Torpedo sinuspersici*, *Torpedo suessii*, *Torpedo tokionis*, *Torpedo torpedo* or common *Torpedo*, and *Torpedo tremens*. Preferably, the cells used are cells of *Torpendo marmorate* or *Topedo californica*.

According to the invention, the step of isolating the membranes can also comprise a step a'), prior to step a), of sampling the *Torpedo* electric tissue. This step of sampling the *Torpedo* electric tissue can be carried out by any method known to those skilled in the art. It may, for example, be the method described in the document Morel et al. (1985) Morel N, Marsal J, Manaranche R, Lazereg S, Mazie J C, Israël M (1985). Large-scale purification of presynaptic plasma membranes from *Torpedo* marmorata electric organ. J. Cell Biol., 101: 1757-1762 [15]. It may be a method comprising, once the *Torpedo* has been anesthetized on a layer of ice, for example by placing the fish on said layer for approximately 20 min, two incisions made at the level of the lateral zones of the head using a scalpel in order to cut the 4 main nerves which connect each electric organ with the *lobus electricus* located behind the cerebellum of the fish. The two electric organs, once removed, are immersed in a buffer solution, comprising, for example, 280 mM of sodium chloride (NaCl), 3 mM of potassium chloride (KCl), 1.8 mM of magnesium chloride ($MgCl_2$), 3.4 mM of calcium chloride ($CaCl_2$), 5 mM of sodium bicarbonate $NaHCO_3$, 1.2 mM of phosphate buffer, 5.5 mM of glucose, 300 mM of urea and 100 mM of sucrose.

According to the invention, the method may also comprise a step a"), prior to step a), of preparing the *Torpedo* electric tissue obtained in step a').

According to the invention, the preparation can be carried out, for example, by immersing the sampled electric tissue in an extraction solution, for example an electrocyte membrane extraction buffer (EMEB) comprising 50 mM of Tris-HCl (pH 7.5), 3 mM of EDTA, 1 mM of ethylene glycol tetraacetic acid (EGTA) and protease inhibitors.

The tissue may then be finely cut up, for example to a thickness of 1 to 5 mm, using a scalpel, and immersed in a freshly prepared solution, for example the EMEB buffer comprising 50 mM of Tris-HCl (pH 7.5), 3 mM of EDTA, 1 mM of ethylene glycol tetraacetic acid (EGTA) and protease inhibitors.

According to the invention, the immersion solution can be prepared extemporaneously, for example during the day, for example 10 hours beforehand, for example 5 hours beforehand, for example 2 hours beforehand.

According to the invention, the step of isolating membranes from the electric organs sampled and prepared as previously described can be carried out by sedimentation, for example in a discontinuous sucrose gradient, for example according to the method described in the document Hill et al. (1991) Hill J A, Nghiêm H-O & Changeux J-P (1991). Serine-specific phosphorylation of nicotinic receptor associated 43K protein. Biochemistry, 30, 5579-5585 [16] or Vilariho et al. (2009) Vilariho N, Fonfria E S, Molgô J, Arâoz R, Botana L M (2009). Detection of Gymnodimine-A and 13-Desmethyl C Spirolide Phycotoxins by Fluorescence Polarization. Analytical Chemistry, 81: 2708-2714 [13]. For example, a tissue prepared, for example as described in step a"), is homogenized in a buffer, for example EMEB as previously defined, using a knife mill, and then the total membrane fraction is precipitated by centrifugation, for example at 20 000 revolutions per minute, and taken up in a buffer, for example EMEB, containing 10% to 45% of sucrose, preferably 35% of sucrose. The discontinuous sucrose gradient can be prepared, for example, with two sucrose solutions from 60% to 10%, prepared in the EMEB buffer, by weight relative to the total weight of the solution, for example two solutions at 60% and 20%, at 30% and 50%, at 35% and 45% of sucrose. According to the invention, one of the sucrose solutions can comprise the *Torpedo* electrocyte total membranes. For example, they may be two sucrose solutions at 35% and at 45%, the 35% sucrose solution containing the *Torpedo* electrocyte total membranes. After ultracentrifugation, the electrocyte membranes sediment at the interphase between the 35% and 45% sucrose solutions, from where they are recovered and washed by ultracentrifugation, for example from 20 000 to 40 000, preferably at 40 000, revolutions per minute in 5 mM glycine buffer.

In another embodiment, after ultracentrifugation, for example from 20 000 to 40 000, preferably at 40 000, revolutions per minute for, for example, 1 to 5 hours, preferably for 3 h, the electrocyte membranes sediment at the interphase between the 35% and 45% sucrose solutions, from where they are recovered and washed by ultracentrifugation, for example from 20 000 to 40 000, preferably at 40 000, revolutions per minute for, for example, from 1 to 60 minutes, preferably for 30 min, in 5 mM glycine buffer.

According to the invention, the *Torpedo* membranes may be electrocyte cell membranes, and are preferably prepared from electrocyte cells of *Torpedoes* previously indicated.

The *Torpedo* electrocyte membranes are membranes comprising nicotinic acetylcholine receptors (nAChRs), in particular muscle-type receptors which consist of two alpha 1 subunits, one beta 1 subunit, one gamma subunit and one delta subunit ($\alpha(1)2\beta\gamma\delta$) (Changeux J P (2010). Allosteric receptors: from electric organ to cognition. Annu. Rev. Pharmacol. Toxicol., 50:1-38 [17]).

The *Torpedo* electrocyte membranes are rich in nAChR, representing from 10% to 60%, from 20% to 60% and preferably from 20% to 40% of the total protein concentration.

According to the invention, the fragmentation of the electrocyte membranes can be carried out by mechanical fragmentation, for example using a grinder, for example a glass grinder, for example a borosilicate glass grinder of Potter-Elvehjem type with a Teflon pestle, or by ultrasound fragmentation, for example by sonication. Preferably, the grinder is a borosilicate glass grinder of Potter-Elvehjem type with a Teflon pestle, for example in 1 to 10 mM glycine buffer, preferably 5 mM glycine buffer. Advantageously, the use of a glass/Teflon grinder makes it possible to preserve the functionality of the nAChRs.

According to the invention, the preparation of the stock solutions of membrane fragments can be carried out by any method known to those skilled in the art. It can, for example, involve placing in solution the fragments isolated according to the method previously described, for example with a Potter-Elvehjem grinder, in a solution comprising from 1 to 10 mM of glycine, preferably 5 mM glycine.

According to the invention, the protein concentration of the stock solution of *Torpedo* electrocyte membrane fragments may be, for example, from 0.5 to 10 mg/ml. According to the invention, the total protein concentration of the *Torpedo* membranes can be adjusted, for example, to a concentration of from 0.5 to 5, from 1 to 4, from 1.5 to 3.5 and preferably from 2.5 to 3.5 mg/ml of protein.

According to the invention, the solution comprising the membrane fragments for coating the plates may be a solution with a pH between from 6.5 to 10, this solution corresponding to the solution into which the membrane fragments are incorporated. It may, for example, be a tris buffered saline (TBS) solution comprising 150 mM sodium chloride, 50 mM Tris-HCl or Tris, pH 7.5, a phosphate buffered saline (PBS) solution comprising 130 mM sodium chloride, 10 mM sodium phosphate, pH 7.0, or a carbonate/bicarbonate buffer solution comprising 150 mM sodium chloride, 100 mM sodium carbonate, pH 9.5.

Advantageously, the pH of the solution comprising the membrane fragments for the coating makes it possible to promote the interaction between the ligand and the nAChR. In addition, the pH of the coating solution advantageously makes it possible to stabilize the membrane fragments, and for the membranes attached to be biologically active.

According to the invention, the total protein concentration in said coating solution with a pH between from 6.5 to 10 may be between from 5 to 200 mg/ml.

According to the invention, the ionic strength of the solution comprising the membrane fragments for coating the plates may be from 0.1 to 0.7 and preferably from 0.16 to 0.42.

According to the invention, the calculation of the ionic strength of the solution can be carried out by any method known to those skilled in the art. For example, it may be the result obtained from the following formula (I):

$$I = \frac{1}{2}\sum_i z_i^2 [x_i] \qquad (I)$$

wherein z represents the charge of the ion i present in said solution at a molar concentration [Xi].

Advantageously, the ionic strength of the solution comprising the membrane fragments for the coating promotes the interaction between the ligand and the nAChR. In addition, the ionic strength of the coating solution advantageously makes it possible to stabilize the membrane fragments, and for the membranes attached to be biologically active.

According to the invention, the attaching of the membrane fragments may be carried out, for example, by non-covalent and nonionic interaction between the membrane fragments and the surface.

According to the invention, the method of the invention may comprise, prior to the attaching step d), a step c') of diluting the membrane fragments in a solution.

According to the invention, the dilution may be carried out, for example, in a physiological solution, for example a saline solution, for example of a tris buffered saline (TBS) solution, comprising 150 mM sodium chloride, 50 mM Tris-HCl, pH 7.5, or of a phosphate buffered saline (PBS) solution comprising 130 mM sodium chloride, 10 mM sodium phosphate, pH 7.0, or a carbonate/bicarbonate buffer solution comprising 150 mM sodium chloride, 100 mM sodium carbonate, pH 9.5.

According to the invention, the device may be any device known to those skilled in the art for attaching biological molecules; for example, it may be a device, the surface of which is made of plastic. It may, for example, be a multiwell plate, for example a 6-, 12-, 24-, 48-, 96- or 384-well plate, preferably a 96- or 384-well plate, a 4-, 8- or 12-well plate or 6-, 8- or 12-well strips. It may, for example, be an ELISA plate, a high-adhesion plate for polar molecules, for example plates of Nunc Polysorp™ (trade mark), Medisorp™ (trade mark), Maxisorp™ (trade mark) or Multisorp™ (trade mark) type. It may, for example, be high-adhesion plates for glycoproteins (the list of microplates is not limiting).

Preferably, the plate is a Maxisorp™ (trade mark) plate. Advantageously, the Maxisorp™ (trade mark) plate has, in addition to hydrophobic groups, many hydrophilic groups increasing its capacity for forming hydrogen bonds in addition to van der Waals interactions (Esser P (2010). Principles in Adsorption to Polystyrene. Technical Bulletin: 06a. Thermo Fisher Scientific Inc. [18]).

According to the invention, when a multiwell plate is used, the amount of protein of the membrane fragments may be from 0.5 to 5 µg of protein per well, for example from 1 to 2 µg of protein per well, from 1 to 1.5 µg of protein per well.

According to the invention, the method can be carried out, for example, with stock solutions of *Torpedo* electrocyte membranes.

According to the invention, the method may be carried out with stock solutions previously obtained, for example, by carrying out steps a) to c) of the method of the invention.

According to the invention, the stock solution may be any solution known to those skilled in the art which is suitable for the storage of membrane fragments, for example a physiological solution, for example TBS, PBS, a glycine solution, for example a glycine solution at a concentration of from 1 mM to 10 mM, from 3 to 8 mM, preferably 5 mM.

In this case, the method of the invention comprises step d) of fixing the membranes using stock solutions.

According to the invention, the stock solutions may be aliquoted beforehand; for example, they may be solutions having a volume of from 10 µl to 1 ml, for example from 100 µl to 500 µl and preferably of 500 µl.

According to the invention, the protein concentration in the stock solution may be between from 0.5 to 5, from 1 to 4, from 1.5 to 3.5 mg/ml, and preferably from 2.5 to 3.5 mg/ml of protein.

Advantageously, the protein concentration makes it possible to avoid in particular repeated thawing/freezing of the membrane samples and thus preserves the functionality of the nAChRs.

Advantageously, the storage of the *Torpedo* electrocyte membrane fragments in aliquots also makes it possible to avoid in particular repeated thawing/freezing of the membrane samples and thus preserves the functionality of the nAChRs.

According to the invention, the attaching step d) can be carried out for a predetermined time; for example, this step can be carried out for at least 10 minutes and preferably at least 60 minutes; for example, step d) can be carried out for 1 to 30 hours, for example from 1 h to 30 h, from 3 h to 24 h, from 6 h to 12 h. Step d) can also be carried out overnight, for example for from 16 to 18 hours.

Advantageously, the duration of step d) makes it possible to stabilize the attachment of the *Torpedo* electrocyte membrane fragments to the surface of the wells, thus increasing the detection sensitivity of the device. This stabilization advantageously allows said devices to be transported by air or overland, for example in Europe or to other continents without impairment of the sensitivity of the method of the present invention and of the device for carrying out said method.

According to the invention, when a stock solution is used in the method of the invention, said method may comprise step c') of diluting the stock solution.

According to the invention, the dilution of the stock solution may be from 50 to 500-fold, preferably from 100 to 300-fold, and even more preferably from 200-fold to 250-fold.

According to the invention, the dilution of the solution can make it possible to obtain, for example, a total protein concentration in the *Torpedo* electrocyte membrane fragments of from 5 µg/ml to 200 pg/ml and preferably from 10 µg/ml to 20 µg/ml of total protein per well.

According to the invention, the dilution of the solution can also make it possible to obtain, for example, a total protein concentration in the *Torpedo* electrocyte membrane fragments of from 1 µg/ml to 200 pg/ml and preferably from 5 µg/ml to 100 µg/ml of total protein per well.

Preferably, when the method is carried out with stock solutions of *Torpedo* electrocyte membranes, they may be stock solutions diluted as previously indicated.

The subject of the present invention is also an analysis device obtained by means of the method according to the invention.

The subject of the present invention is also the use of an analysis device according to the invention for detecting and quantifying toxins, for example neurotoxins.

According to the invention, the neurotoxins may be any neurotoxins known to those skilled in the art; for example, they may be neurotoxins which act, for example, on nicotinic acetylcholine receptors, neurotoxins produced by marine phytoplankton, such as certain members of the *Alexandrium* genus, for example *Alexandrium ostenfeldii*, producing, for example, spirolide, members of the *Karenia* genus, for example *Karenia selliformis*, producing, for example, gymnodimine, phycotoxins of the spiroimine family, for example pinnatoxins, pteriatoxins, prorocentrolides or spiro-prorocentrimine, which may be produced by various phytoplankton species (Molgô J, Girard E, Benoit E. (2007) Cyclic imines: an insight into this emerging group of bioactive marine toxins. *In Phycotoxins: Chemistry and Biochemistry* (Botana, L. M., ed) pp. 319-335, Blackwell Publishing Ltd, Iowa [4]). They may also be cyanobacterial neurotoxins, for example anatoxin-a or homoanatoxin-a, produced, for example, by members of the *Anabaena, Aphanizomenon, Cylindrospermum, Microcystis, Oscillatoria, Phormidium, Planktothrix* and *Raphidiopsis* genera, or pinnamine, a marine toxin with a chemical structure very close to anatoxin-a, and/or any toxin capable of acting on nAChRs (Arâoz R, Molgô J, Tandeau de Marsac N T (2009) Neurotoxic cyanobacterial toxins. Toxicon 56: 813-828 [19], (Molgô J, Girard E, Benoit E. (2007) Cyclic imines: an insight into this emerging group of bioactive marine toxins. In Phycotoxins: Chemistry and Biochemistry (Botana, L. M., ed) pp. 319-335, Blackwell Publishing Ltd, Iowa [4]).

The subject of the present invention is also the use of an analysis device according to the invention for detecting and quantifying nicotinic acetylcholine receptor ligands.

The subject of the present invention is also the use of an analysis device according to the invention for the high-throughput screening of nicotinic acetylcholine receptor ligands.

The present invention advantageously makes it possible to increase the efficiency of coating of *Torpedo* membrane fragments on surfaces, for example microplates and/or strips, by virtue, for example, of the choice of the pH and of the ionic strength of said solutions and/or the choice of the incorporating solutions and of the components of said coating solutions. In addition, the present invention takes advantage of the development of surface chemistry seeking to maximize the degree of attachment of proteins by plastic microplates (Esser P (2010). Principles in Adsorption to Polystyrene. Technical Bulletin: 06a. Thermo Fisher Scientific Inc. [18]). In addition, increasing the attachment, for example on Maxisorp™ plates, can involve the surface chemistry of said plates and the macromolecular nature of the *Torpedo* membranes. Indeed, the *Torpedo* electrocyte membrane fragments are mixtures of lipids (membranes) and of proteins, of which the nAChR may represent up to 40% of the total protein concentration. In addition, nAChRs are highly glycosylated proteins (7.5%) (Da Costa C J B, Kaiser D E E, Baenziger J E (2005). Role of Glycosylation and Membrane Environment in Nicotinic Acetylcholine Receptor Stability. Biophys J, 88, 1755-1764 [20]), which thus reinforces the efficiency of the attachment and the coating of the surface, for example of Maxisorp™ plates, by virtue of noncovalent interactions and the formation of a hydrogen bridge between the nAChR-rich electrocyte membranes and the surface.

Advantageously, in the present invention, the attaching of nAChR-rich electrocyte cell membranes allows the detection of small amounts, for example of the order of a nanogram or even of a picogram, of substances, for example of neurotoxins as previously indicated.

The subject of the present invention is also the use of an analysis device according to the invention for the physico-chemical purification and characterization of nicotinic acetylcholine receptor ligands.

Advantageously, the present device may also be used in order to purify and identify nicotinic acetylcholine receptor (nAChR) ligands.

Advantageously, the strong adhesion of the *Torpedo* electrocyte membrane fragments on the surface of the plates as defined above, for example the plates of Maxisorp™ (trademark) type, or of high-adhesion plates for glycoproteins and membranes with a high protein concentration, makes it possible to attach and trap at least one or more ligands which interact(s) with *Torpedo* nAChRs.

The recovery of the attached ligand(s) can be carried out, for example, after washing the device according to the invention with a washing buffer, for example Tris buffered saline (TBS) containing 0.1% Tween 20, via a step of eluting with an eluting solution, for example methanol in the case of lipophilic molecules, such as cyclized imines, or by using other buffers with an ionic strength, pH and detergent concentration, predetermined by those skilled in the art, which can release the ligands from the *Torpedo* nAChR.

Once the ligands have been eluted, their chemical nature can be rapidly determined, for example in a time of approximately 5 minutes, for example using mass spectrometry, of MALDI-TOF-MS type and/or any method known to those skilled in the art.

Advantageously, according to the invention, the *Torpedo* electrocyte membrane fragments do not need to be chemically modified in order to attach strongly to the surface of the plates. The present invention therefore advantageously allows the attachment of the membrane fragments without prior structural modification and advantageously makes it possible not to denature or impair the biological properties of said membrane fragments.

Other advantages may become further apparent to those skilled in the art on reading the examples below, illustrated by the appended figures, given by way of illustration.

BRIEF DESCRIPTION OF THE FIGURES

FIG. 2 A represents curves of saturation of the binding between biotin-α-BgTx and the *Torpedo* electrocyte nAChRs using 500-fold diluted membrane solutions (-▼-), 200-fold diluted membrane solutions (-●-), 100-fold diluted membrane solutions (-■-) and 50-fold diluted membrane solutions (-▲-). Each dilution was carried out in Tris buffered saline (TBS). The membranes were incubated overnight with various concentrations of biotin-α-BgTx ($5\times10^{-12}$ M to $5\times10^{-6}$ M) in order to determine the affinity constant of the biotin-α-BgTx for the *Torpedo* nAChR.

FIG. 2 B is a diagram representing the determination of the concentration of tracer (biotin-α-BgTx) for the method. The microplate wells having been coated with a solution of *Torpedo* electrocyte membranes diluted 200-fold in TBS buffer were incubated with various concentrations of biotin-α-BgTx: $2\times10^{-9}$ M (-▼-), $6\times10^{-9}$ M (-▽-), $1\times10^{-8}$ M (-■-), $4\times10^{-8}$ M (-□-), $8\times10^{-8}$ M (-●-) and $2\times10^{-7}$ M (-○-) for 0, 0.5, 1, 1.5 and 2 h. The x-axis represents the incubation time in hours (h) and the y-axis the optical density measured at a wavelength of 492 nm ($OD_{492\ nm}$).

FIG. 2 C is a diagram representing the determination of the dilution of *Torpedo* electrocyte membranes for the ligand-receptor binding displacement test on an ELISA microplate. Various dilutions of *Torpedo* electrocyte membrane (10 to 5000-fold diluted) were incubated overnight with $8\times10^{-8}$ M of biotin-α-BgTx. The x-axis represents the membrane dilution (1/X) and the y-axis the optical density measured at a wavelength of 492 nm ($OD_{492\ nm}$). All the experiments were carried out at least twice. Each point of the curve represents the mean value±mean deviation (n=3).

FIG. 3 A is a photograph of a microplate showing the dose-dependent competitive inhibition of the biotin-α-BgTx binding with *Torpedo* nAChRs by standard α-BgTx and by the phycotoxin 13-desmethyl spirolide C. Each dose was tested in triplicate. Represented on the left-hand part is the concentration of α-BgTx/(well): $3.3 \times 10^{-6}$ (A1-A3), $1.1 \times 10^{-6}$ (B1-B3), $3.7 \times 10^{-7}$ (C1-C3), $1.2 \times 10^{-7}$ (D1-D3), $4.1 \times 10^{-8}$ (E1-E3), $1.4 \times 10^{-8}$ (F1-F3), $4.6 \times 10^{-9}$ (G1-G3), $1.5 \times 10^{-9}$ (A4-A6), $5.1 \times 10^{-10}$ (B4-B6), $1.7 \times 10^{-10}$ (C4-C6), $5.7 \times 10^{-11}$ (D4-D6), $1.9 \times 10^{-11}$ (E4-E6), $6.2 \times 10^{-12}$ (F4-F6) and $2.09 \times 10^{-12}$ M α-BgTx (G4-G6). Represented on the right-hand part is the concentration of 13-desmethyl SPX C/(well): $3.3 \times 10^{-7}$ (A7-A9), $1.1 \times 10^{-7}$ (B7-B9), $3.7 \times 10^{-8}$ (C7-C9), $1.2 \times 10^{-8}$ (D7-D9), $4.1 \times 10^{-9}$ (E7-E9), $1.4 \times 10^{-9}$ (F7-F9), $4.6 \times 10^{-10}$ (G7-G9), $1.5 \times 10^{-10}$ (A10-A12), $5.1 \times 10^{-11}$ (B10-B12), $1.7 \times 10^{-11}$ (C10-C12), $5.7 \times 10^{-12}$ (D10-D12), $1.9 \times 10^{-12}$ (E10-E12), $6.2 \times 10^{-13}$ (F10-F12) and $2.1 \times 10^{-13}$ M 13-desmethyl SPX C (G10-G12). The α-BgTx and 13-desmethyl SPX C competitively inhibit in a dose-dependent manner, but on a different scale, the binding of biotin-α-BgTx to the nAChR of the immobilized *Torpedo* membranes. The plate signal is the negative control: wells not coated with the membranes. 100% signal is the positive control: wells in which *Torpedo* membranes have been placed, in the absence of toxins or of extract samples.

FIG. 3 B is a diagram representing the dose-dependent inhibition of the biotin-α-BgTx binding with immobilized *Torpedo* nAChRs using the test for ligand-receptor binding displacement, on an ELISA microplate, by α-BgTx (-●-), 13,19-didesmethyl spirolide C (-○-), 13-desmethyl spirolide C (-■-) and by gymnodimine A (-□-). Independent experiments were carried out at least three times. Each point represents the mean value±mean deviation (n=3). The x-axis represents the toxin concentration (M) and the y-axis the percentage inhibition.

FIG. 4 represents the competitive inhibition of the biotin-α-BgTx binding with the *Torpedo* nAChR by phycotoxins bearing cyclized imines and control and contaminated seafood extracts.

FIG. 4 A is a photograph of a microplate showing the dose-dependent competitive inhibition of the biotin-α-BgTx binding with *Torpedo* nAChRs by 13-desmethyl SPX C and seafood extracts contaminated with said toxin and control extracts. Each dose was tested in triplicate. On the left-hand part: concentration of 13-desmethyl spirolide (wells): $1.7 \times 10^{-5}$: (A1-A3), $5.6 \times 10^{-6}$: (B1-B3), $1.9 \times 10^{-6}$: (C1-C3), $6.2 \times 10^{-7}$: (D1-D3), $2.1 \times 10^{-7}$: (E1-E3), $6.9 \times 10^{-8}$: (F1-F3), $2.3 \times 10^{-8}$: (G1-G3), $7.6 \times 10^{-9}$: (A4-A6), $2.5 \times 10^{-9}$: (B4-B6), $8.5 \times 10^{-10}$: (C4-C6), $2.8 \times 10^{-10}$: (D4-D6), $9.4 \times 10^{-11}$: (E4-E6), $3.1 \times 10^{-11}$: (F4-F6) and $1.0 \times 10^{-11}$ M 13-SPX-C: (G4-G6). Represented on the right-hand part is the concentration of 13-desmethyl spirolide of $3.5 \times 10^{-12}$ M (A7-A9) and the seafood extracts. Seafood extracts doped with 13-desmethyl spirolide C-dilution: (wells). Queen scallops-$D_{200}$: (B7-B9), Queen scallops-$D_{400}$: (C7-C9), oysters-$D_{200}$: (D7-D9), oysters-$D_{400}$: (E7-E9), mussels-$D_{200}$: (F7-F9), mussels-$D_{400}$: (G7-G9), scallops-$D_{200}$: (A10-A12) and scallops-$D_{400}$: (B10-B12). Control seafood extracts-dilution: (wells). Control Queen scallops-$D_{200}$: C10-C12), control oysters-$D_{200}$: (D10-D12), control mussels-$D_{200}$: (E10-E12), control scallops-$D_{200}$: (F10-F12) and control scallops-$D_{400}$: (G10-G12). Plate signal: negative control wells incubated with no coating by a membrane (H1-H3); 100% signal: positive control wells in which *Torpedo* membranes were incubated without toxins or without extract (H4-H9); 100% inhibition: wells comprising *Torpedo* membranes incubated with $1 \times 10^{-5}$ M of α-BgTx (H10-H12).

FIG. 4 B is a photograph of a microplate showing the dose-dependent competitive inhibition of the biotin-α-BgTx binding with *Torpedo* nAChRs by gymnodimine-A, seafood extracts contaminated with said toxin and control extracts. Each dose was tested in triplicate. On the left-hand part: concentration of gymnodimine-A (wells): $1.7 \times 10^{-5}$: (A1-A3), $5.6 \times 10^{-6}$: (B1-B3), $1.9 \times 10^{-6}$: (C1-C3), $6.2 \times 10^{-7}$: (D1-D3), $2.1 \times 10^{-7}$: (E1-E3), $6.9 \times 10^{-8}$: (F1-F3), $2.3 \times 10^{-8}$: (G1-G3), $7.6 \times 10^{-9}$: (A4-A6), $2.5 \times 10^{-9}$: (B4-B6), $8.5 \times 10^{-10}$: (C4-C6), $2.8 \times 10^{-10}$: (D4-D6), $9.4 \times 10^{-11}$: (E4-E6) and $3.1 \times 10^{-11}$ M GYM-A: (F4-F6). Extracts of Queen scallops doped with GYM A-dilution: (wells). Queen scallops-$D_{200}$: (G4-G6). Right-hand side: seafood extracts doped with GYM A-dilution: (wells). Queen scallops-$D_{400}$: (A7-A9), oysters-$D_{200}$: (B7-B9), oysters-$D_{400}$: (C7-C9), mussels-$D_{200}$: (D7-D9), mussels-$D_{400}$: (E7-E9), scallops-$D_{200}$: (F7-F9) and scallops-$D_{400}$: (G7-G9). Control seafood extracts-dilution: (wells). Control Queen scallops-$D_{200}$: (H7-H9), control Queen scallops-$D_{400}$: (A10-A12), control oysters-$D_{200}$: (B10-B12), control oysters-$D_{400}$: (C10-C12), control mussels-$D_{200}$: (D10-D12), control mussels-$D_{400}$: (E10-E12), control scallops-$D_{200}$: (F10-F12) and control scallops-$D_{400}$: (G10-G12). Plate signal: (H1-H3); 100% signal: (H4-H6); 100% inhibition: (H10-H12).

FIG. 4 C is a photograph of a microplate showing the dose-dependent competitive inhibition of the biotin-α-BgTx binding with *Torpedo* nAChRs by 13,19-didesmethyl spirolide C, seafood extracts contaminated with said toxin and control extracts. Each dose was tested in triplicate. On the left-hand part: concentration of 13,19-didesmethyl spirolide C (wells): $3.3 \times 10^{-7}$ M (A1-A3), $1.1 \times 10^{-7}$ M (B1-B3), $3.7 \times 10^{-8}$ M (C1-C3), $1.2 \times 10^{-8}$ M (D1-D3), $4.1 \times 10^{-9}$ M (E1-E3), $1.4 \times 10^{-9}$ M (F1-F3), $4.6 \times 10^{-10}$ M (G1-G3), $1.5 \times 10^{-10}$ M (A4-A6), $5.1 \times 10^{-11}$ M (B4-B6), $1.7 \times 10^{-11}$ M (C4-C6), $5.7 \times 10^{-12}$ M (D4-D6), $1.9 \times 10^{-12}$ M (E4-E6), $6.2 \times 10^{-13}$ M (F4-F6) and $2.1 \times 10^{-13}$ M 13-19-SPX C (G4-G6). Right-hand side: seafood extracts doped with 13,19-didesmethyl spirolide C-dilution: (wells). Queen scallops-$D_{200}$: (A7-A9), Queen scallops-$D_{400}$: (B7-B9), mussels-$D_{200}$: (C7-C9), mussels-$D_{400}$: (D7-D9), oysters-$D_{200}$: (E7-E9), oysters-$D_{400}$: (F7-F9), scallops-$D_{200}$: (G7-G9) and scallops-$D_{400}$: (A10-A12). Control seafood extracts-dilution: (wells). Control Queen scallops-$D_{200}$: (B10-B12), control oysters-$D_{200}$: (C10-C12), control mussels-$D_{200}$: (D10-D12), control scallops-$D_{200}$: (E10-E12). Cyanobacterial extracts-dilution: (wells). PCC 6506-$D_{100}$: (F10-F12) and PCC 101 11-$D_{100}$: (G10-G12). Plate signal: (H1-H3); 100% signal: (H4-H9); 100% inhibition: (H10-H12).

FIG. 4D is a column diagram representing the matrix effect. Seafood homogenates (Queen scallops=A; oysters=H; mussels=M and scallops=S) were doped with 13,19-didesmethyl spirolide C, 13-desmethyl spirolide C and gymnodimine A. The results were obtained with the ligand-receptor binding displacement test on an ELISA microplate. The columns represent the mean value±standard error of the mean (n=3 for the doped samples and n=9 for the control seafood samples). The x-axis represents the samples tested and the y-axis the percentage inhibition. 13,19-SPX C=13,19-didesmethyl spirolide C, 13-SPX C=13-desmethyl spirolide C, GYM=gymnodimine A.

FIG. 5 represents the screening of the nAChR competitive ligands/toxins using extracts of marine cyanobacteria, by employing the ligand-receptor binding displacement test on an ELISA microplate with a 96-tip manual pipetting device.

FIG. 5 A is a photograph of the 96-tip manual pipetting device showing the loading and pipetting zones.

FIG. 5 B represents the plate plan for the screening of nAChR competitive ligands/toxins using the extracts of marine cyanobacteria I to VII, employing 13,19-SPX C (VIII) as positive control. PS (plate signal), 100% (100% signal). BgTx (1×10$^{-6}$ M α-bungarotoxin: 100% inhibition).

FIG. 5 C is a photograph of a microplate showing the screening of nAChR competitive ligands/toxins using the extracts of marine cyanobacteria I to VII tested at three dilutions: $D_{10}$: first row, $D_{100}$: second row and $D_{1000}$, third row. The rectangle VIII shows, on the same plate, the dose-dependent competitive inhibition of the biotin-α-BgTx binding with *Torpedo* nAChRs by 13,19-didesmethyl spirolide C: first row: 5×10$^{-7}$ M, second row: 5×10$^{-8}$ M, third row: 5×10$^{-9}$ M, fourth row: 5×10$^{-10}$ M, fifth row: 5×10$^{-11}$ M, sixth row: 5×10$^{-12}$ M and seventh row: 5×10$^{-13}$ M. Plate signal: (H1-H3); 100% signal: (H4-H9); 100% inhibition: (H10-H12).

EXAMPLES

Example 1: Method for Detecting the Interaction Between Nicotinic Acetylcholine Receptors (nAChRs) and Toxins Products Used In the example below, the products and devices used were the following:

The flat-bottomed Maxisorp ELISA plates were purchased from the company Nunc (Kamstrupvej, Denmark).

The coating buffer was the following: tris buffered saline (TBS) (150 mM sodium chloride, 50 mM Tris-HCl, pH 7.5).

Washing buffer: TBS containing 0.1% Tween 20.

Blocking buffer: TBS containing 0.5% bovine serum albumin (BSA).

A 10-times concentrated TBS buffer stock solution at pH 7 was prepared and was autoclaved and stored at ambient temperature, namely 25° C., for preparing said buffers.

The biotinylated α-bungarotoxin (biotin-α-BgTx) was purchased from the company Molecular Probes (Eugene, Oreg., USA).

The Complete Protease Inhibitor mix was purchased from the company Roche Diagnostics GmbH, Mannheim, Germany. The bovine serum albumin (BSA) came from the company Sigma-Aldrich (St. Louis, Mo., USA). The peroxidase-coupled streptavidin was purchased from the company Sigma-Aldrich. The o-phenylenediamine dihydrochloride tablets were purchased from the company Dako (Glostrup, Denmark). The α-bungarotoxin was purchased from the company Sigma-Aldrich. The 13-desmethyl spirolide C was purchased from the company NRC-CNRC (Institute for Marine Biosciences, National Research Counsel, Halifax, NS, Canada). The gymnodimine A was purchased from the company NRC-CNRC. The 13,19-didesmethyl spirolide C was purchased from the company CIFGA (Lugo, Spain). The anatoxin-a came from the company Tocris (Ellisville, Mo., USA).

Figure 1:
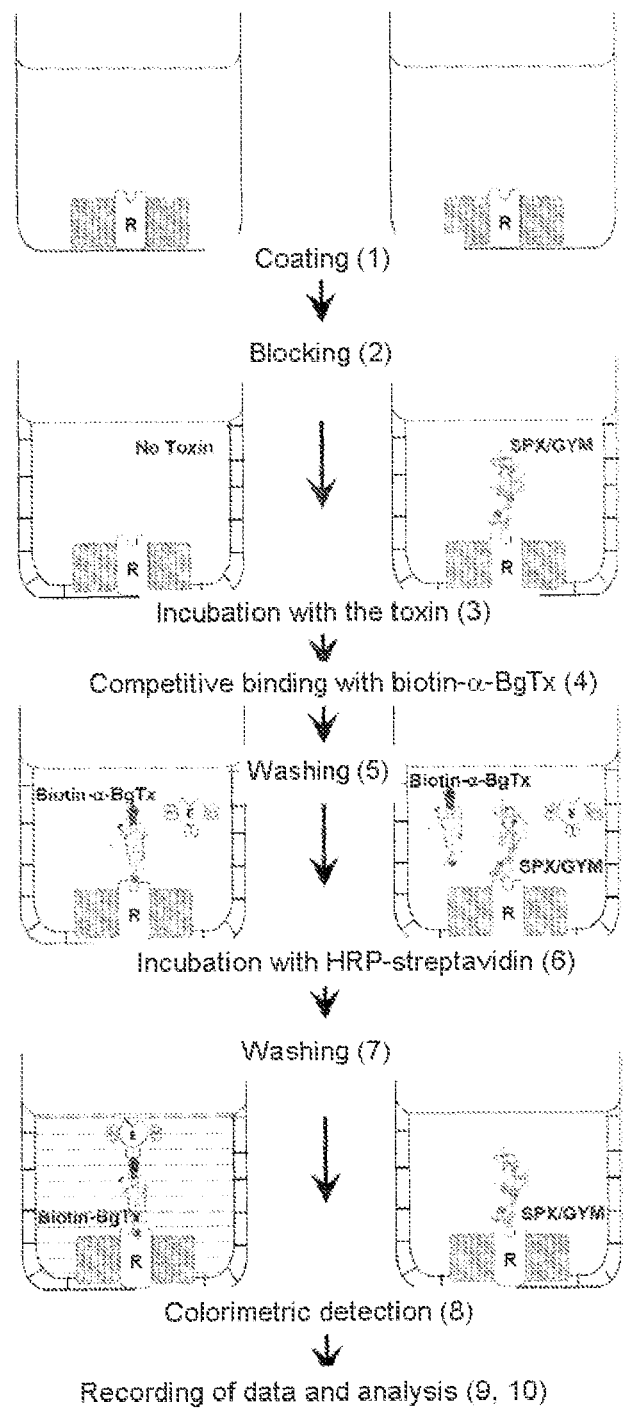
FIG. 1 represents a diagram of the ligand-receptor binding displacement test on an ELISA microplate. The diagram represents the various steps of the method: (1) coating of the microplate wells with *Torpedo* electrocyte membranes rich in nicotinic acetylcholine receptors (nAChRs), (2) blocking of the unbound plastic surfaces, (3) incubation of the *Torpedo* membranes immobilized on the wall of the wells with a test solution (either standard toxin or seafood extract), (4) competitive displacement of the ligand bound to the receptor by biotin-α-bungarotoxin (biotin-α-BgTx), (5) washing, (6) incubation with streptavidin coupled to horseradish peroxidase (HRP-streptavidin), (7) washing, (8) colorimetric detection of the HRP-streptavidin-biotin-α-BgTx-nAChR complex, (9) reading of the ELISA plate and analysis of the data. Abbreviations: R=nAChR, SPX=13-desmethyl spirolide C/13,19-didesmethyl spirolide C, GYM=gymnodimine A, biotin-α-BgTx=biotin-α-bungarotoxin, E=HRP-streptavidin.

Protocol:

FIG. 1 represents the various stages of implementation of the method.

Coating with the Membranes

A Nunc Maxisorp™ 96-well flat-bottomed ELISA plate was coated with 100 μl per well of *Torpedo* electrocyte membranes, the total protein concentration of which was 13.5 μg/ml in TBS coating buffer (150 mM NaCl, 50 mM Tris-HCl, pH 7.5, i.e. 1.35 μg of protein per well). The plates were closed and incubated at ambient temperature (25° C.) for 2 hours or overnight at 4° C.

The stock solution of membranes was diluted 200-fold in TBS buffer before the coating of the plates. The coating was carried out with an eLINE multichannel electronic pipetting device (Biohit, Helsinki, Finland) which made it possible to accelerate the loading of the membranes. Three wells were left without coating with membranes so that they could be used as negative control wells (plate signal).

Blocking

The excess membrane was removed. The residual buffer on the plate was removed with absorbent paper.

Without washing, the wells were filled with 250 μl of blocking buffer (TBS, 0.5% BSA) per well. The plate was closed and incubated for one hour at ambient temperature, namely 25° C.

The plates were stored at 4° C. for subsequent use. Parallel experiments were carried out with plates coated six months beforehand and with plates coated on the previous day: no significant difference was observed between the various plates for the ligand binding dose-response curves (results not represented).

Incubation with the Toxins/Extracts

The blocking buffer was removed and the residual liquid on the top of the plate was absorbed with absorbent paper. Without washing, the plates were loaded either with a) 100 μl of standard toxins prepared in blocking buffer or with b) 100 μl of blocking buffer containing up to 10% of extracts (volume/volume). Each toxin or sample concentration was tested 3 times. The plate was closed and incubated for three hours with constant shaking at ambient temperature (25° C.) or overnight at 4° C. for maximum sensitivity.

Six wells coated with *Torpedo* membranes were left free of toxin or of extract so as to use them as negative controls (100% signal). In addition, three wells coated with *Torpedo* membranes were left free of toxin or extract in order to use them as a nonspecific inhibition control. Said wells are incubated with 1 μM α-bungarotoxin (100% inhibition).

The methanol concentration was kept below 1% in order to avoid any interference with the binding of the ligand to the nAChR.

Biotin-BgTx Displacement:

Without removing the toxins and/or the extracts, 50 μl of biotin-α-BgTx (8×10$^{-8}$ M, final concentration) were added to each well. The plate was closed and the whole was incubated for 30 minutes with constant shaking at ambient temperature (25° C.)

The unbound toxins, extracts or biotin-α-BgTx were removed and the wells were washed three times with 250 μl of washing buffer (TBS, 0.1% Tween 20). The residual buffer was absorbed with absorbent paper.

Streptavidin-Biotin Reaction

An amount of 100 μl of peroxidase-coupled streptavidin (diluted 5000 times, ~220 ng/nl protein, Sigma) was added to each of the wells with an eLINE (registered trade mark) multichannel electronic pipetting device (Biohit). The plate was closed and incubated for 30 minutes at ambient temperature (25° C.) with constant shaking, i.e. shaking of approximately 50 revolutions per minute.

The multichannel electronic pipetting device makes it possible to minimize the differences in exposure times to the reaction between the biotin part of the tracer and the streptavidin part of the enzyme. However, owing to the high affinity between biotin and streptavidin ($K_d$=10$^{-14}$ M), a reaction of 30 minutes gives a negligible effect linked to the difference in exposure time for each row of wells. The reaction time between the biotin-α-BgTx and the streptavidin-peroxidase was determined experimentally, namely *Torpedo* electrocyte membranes immobilized on wells of the Maxisorp™ microplate were incubated with $8 \times 10^{-8}$ M biotin-α-BgTx for 30 minutes at 25° C. After washing, 100 μl of peroxidase-coupled streptavidin (diluted 5000-fold) were added to each well. The incubation time was 0, 1, 2.5, 5, 10, 15 and 30 min. The wells were washed and the peroxidase activity was detected as described below.

Colorimetric Detection

The excess streptavidin-peroxidase was removed and the wells were washed three times with 250 μl of washing buffer (TBS, 0.1% Tween 20). The residual buffer on the plate was removed with absorbent paper. An amount of 100 μl of OPD peroxidase substrate (Dako, Glostrup, Denmark) was added to each well with a multichannel electronic pipetting device. When a suitable color developed, i.e. after approximately 5 minutes of incubation, the enzymatic reaction was stopped by adding 100 μl of 0.5 M $H_2SO_4$ to each well with a multichannel electronic pipetting device.

The use of a multichannel electronic pipetting device makes it possible to avoid variations in the development of the color due to the difference in exposure time. The stopping solution was added in the same order as the peroxidase substrate (OPD) solution was added in order to minimize the differences due to the incubation time.

The peroxidase substrate (OPD) was prepared according to the supplier's recommendations. Four OPD tablets were dissolved in 12 ml of deionized water at ambient temperature (25° C.), following which, 5 μl of 30% hydrogen peroxide were added.

The plate was recorded with an ELISA reader (Genios Pro, Tecan), at an absorbance of 492 nm (FIG. 1).

The percentage inhibition was calculated according to the following formula:

% inhibition=[100×(100% signal−sample signal)/
(100% signal−(100% inhibition−plate signal))].

The 100% signal was obtained in wells in which *Torpedo* membranes were applied and incubated without toxins/extracts; the plate signal was obtained from the wells in which the coating with the *Torpedo* membranes was omitted. Independent experiments were carried out at least twice with triplicates.

The percentage inhibition was also calculated according to the following formula:

% inhibition=[100×(100% signal−sample signal)/
(100% signal−100% inhibition)].

The 100% signal was obtained in wells in which *Torpedo* membranes were applied and incubated without toxins/extracts; the 100% inhibition signal ("100% inhibition") was obtained from the wells in which the *Torpedo* membranes were incubated with α-bungarotoxin (1 or 10 μM). Independent experiments were carried out at least twice with triplicates.

Figure 3:
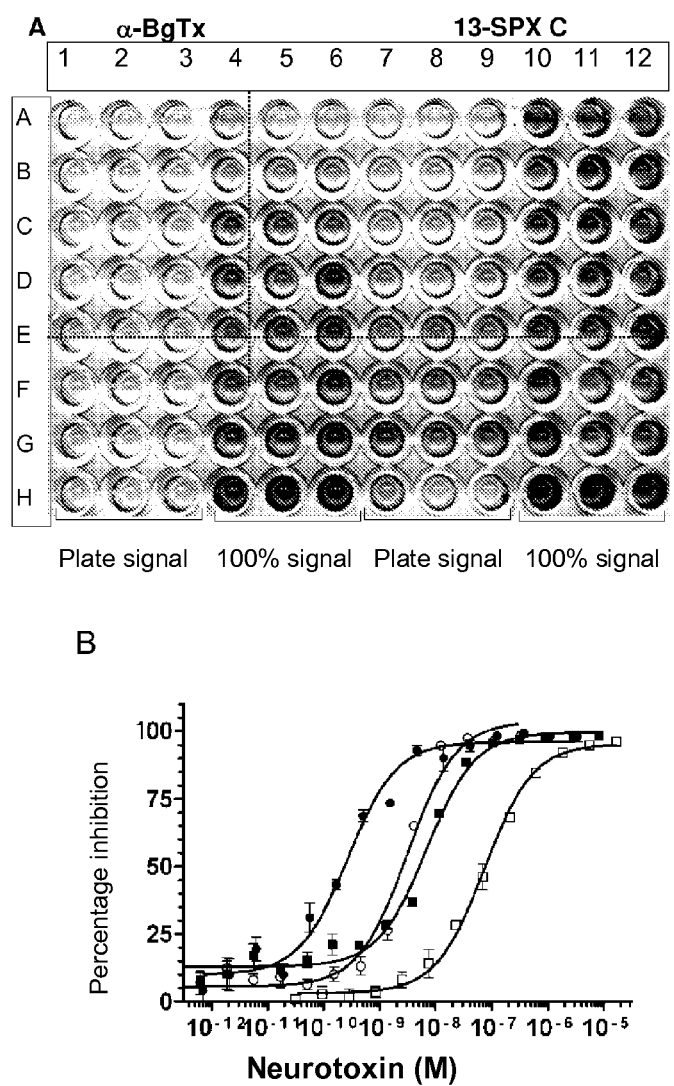
FIG. 3 represents the competitive inhibition of the biotin-α-BgTx binding with the *Torpedo* nAChR by α-bungarotoxin and phycotoxins bearing cyclized imines.

The results showed that nAChR antagonists, namely: α-bungarotoxin, 13-desmethyl spirolide C, 13,19-didesmethyl spirolide C, gymnodimine, d-tubocurarine (curare), and nAChR agonists, namely: anatoxin-a and homoanatoxin-a, inhibit the interaction between α-BgTx and *Torpedo* nAChR in a concentration-dependent manner, with different affinities (FIGS. 3 A, 3 B, 4 A, 4 B and 4 C).

This system is also usable with alkaline phosphatase-coupled streptavidin in addition to the horseradish peroxidase-coupled streptavidin, and, as agents for visualizing the enzymes, substrates either producing a colorimetric reaction (OPD, nitro blue tetrazolium chloride) or which are a substance detectable by chemiluminescence (ECL+) (Arâoz R, Herdman M, Rippka R, Ledreux A, Molgô J, Changeux J P, Tandeau de Marsac N, Nghiêm H O. (2008). A nonradioactive ligand-binding assay for detection of cyanobacterial anatoxins using *Torpedo* electrocyte membranes. Toxicon 52:163-174 [14]). The list of visualizing agents is not limiting.

TABLE 1

Sensitivity of the nonradioactive test for ligand-receptor binding displacement on an ELISA microplate for detecting α-bungarotoxin (α-BgTx), 13-desmethyl spirolide C (13-SPX C), 13,19-didesmethyl spirolide C (13,19-SPX C), gymnodimine A (GYM A) and anatoxin-A (ANTX)

|  | α-BgTx | 13-SPX C | 13,19-SPX C | GYM A | ANTX |
|---|---|---|---|---|---|
| $IC_{50}$ (95% CI) | 0.27 | 6.84 | 3.10 | 74.23 | 68.81 |
|  | (0.18- | (5.07- | (1.98- | (62.4- | (35.3- |
|  | 0.41) | 9.22) | 4.85) | 88.3) | 34.2) |
| LOD (nM) | 0.02 | 1 | 0.8 | 2 | 2 |
| LOQ (nM) | 0.20 | 4 | 2.0 | 20 | 30 |
| $IC_{90}$ (nM) | 70 | 60 | 20 | 2000 | 2000 |

The $IC_{50}$ represents the neurotoxin concentration at which there is 50% inhibition of the binding between the biotin-α-BgTx and the *Torpedo* nAChRs; the 95% CI is the 95% confidence interval of the corresponding $IC_{50}$ value; the LOD is the limit of detection of the method, the LOQ is the limit of quantification of the method; $IC_{90}$ represents the neurotoxin concentration required to inhibit 90% of the binding between the biotin-α-BgTx and the *Torpedo* nAChRs.

The nonradioactive test for ligand-receptor binding displacement on an ELISA microplate is a functional method based on the mechanism of action of competitive nAChR ligands. This method makes it possible to detect competitive nAChR agonists and antagonists with great sensitivity.

The sensitivity of the method using the devices of the present invention was compared with ultra performance liquid chromatography coupled to mass spectrometry (UPLC-MS/MS) for the detection of 13-SPX C, 13,19-SPX C and GYM A [Arâoz et al., manuscript in preparation]. The LOD and LOQ values obtained by UPLC-MS/MS show that the sensitivity of the nonradioactive displacement method using the device of the present invention is in the same order of magnitude as that of UPLC-MS/MS (table 2).

TABLE 2

Sensitivity of UPLC-MS/MS for detecting 13-SPX C, 13,19-SPX C and GYM A

|  | 13-SPX C | 13,19-SPX C | GYM A |
|---|---|---|---|
| LOD (nM) | 4.78 | 1.66 | 1.52 |
| LOQ (nM) | 13.1 | 5.55 | 4.17 |

As demonstrated in this example, the use of the device obtained by means of the method of the invention makes it possible to detect the interaction between nAChRs and ligands with a sensitivity which is as high as the most widely specified techniques of the prior art, without the use of a complex and/or expensive device and in parallel on a large number of samples (96) for the simultaneous detection of the multitude of nAChR ligands/agonists/antagonists, namely spirolides, gymnodimines, pinnatoxins, anatoxins, curare, etc. (the list is not limiting).

Example 2: Method for Detecting 13-Desmethyl Spirolide C, 13,19-Didesmethyl Spirolide C and Gymnodimine A from Seafood Extracts and Anatoxin-A from Cyanobacterial Extracts In this example, the following solutions and protocols were used:
Coating buffer: TBS (150 mM sodium chloride, 50 mM Tris-HCl, pH 7.5).
Dilution of membranes: 200-fold. A volume of 50 μl of *Torpedo* membrane (2.7 $mg \cdot ml^{-1}$ of protein in 5 mM of glycine) was diluted in 10 ml of TBS.

Support: Maxisorp flat-bottomed ELISA plates (Nunc).

Coating volume: 100 μl of *Torpedo* membranes diluted 200-fold.

Coating temperature and time: ambient temperature (25° C.) for 2 hours or 4° C. overnight.

Control seafood (Queen scallops, oysters, mussels and scallops) extracts and seafood (Queen scallops, oysters, mussels and scallops) extracts doped with 13-desmethyl spirolide C, 13,19-didesmethyl spirolide C and gymnodimine A.

Extracts of cyanobacteria producing anatoxin-a and homoanatoxin-a.

A Maxisorp flat-bottomed 96-well ELISA plate (Nunc) was coated with 100 μl per well of a solution of *Torpedo* electrocyte membranes (13.5 μg/ml total protein, i.e. 1.35 μg of membrane protein per well) in TBS buffer (150 mM NaCl, 50 mM Tris-HCl, pH 7.5) using a multichannel pipetting device. The plate was closed and incubated at ambient temperature (25° C.) for 2 hours or at 4° C. overnight.

Detection of Phycotoxins in Seafood Extracts

Extraction of the Lipophilic Toxins from Seafood:

The preparation of the crude extracts from seafood samples was carried out as follows: Queen scallop, oyster, mussel or scallop flesh (100 g) was homogenized in a knife mill at maximum power and divided up into 10 aliquots and kept at −80° C.

50 μl of standard 13-desmethyl spirolide C, 50 μl of standard 13,19-didesmethyl spirolide C or 50 μl of standard gymnodimine A, all three at a concentration of 10 μM, were added separately to 1 g of each seafood homogenate.

In order to extract these lipophilic phycotoxins, 4 ml of acetone were added to each of the doped homogenates. The mixtures were vortexed for 10 seconds and mixed on a rotary mechanical shaker for 15 minutes at ambient temperature (25° C.). The homogenates were then centrifuged at 3500 g for 15 minutes at 4° C. and the supernatants were recovered, whereas the pellets were re-extracted twice with 4 ml of acetone as has just been described. The supernatant pools were evaporated and the residues were resuspended in 4 ml of water. 4 ml of hexane were added to the aqueous extracts and left for 30 min at ambient temperature (25° C.) in order for the chemical partitioning to take place.

Alternatively, the homogenates were centrifuged at 3500 revolutions per minute for 15 minutes at 4° C. and the supernatants were recovered, whereas the pellets were re-extracted twice with 4 ml of acetone as has just been described. The supernatant pools were evaporated and the residues were resuspended in 4 ml of water. 4 ml of hexane were added to the aqueous extracts and left for 30 min at ambient temperature (25° C.) in order for the chemical partitioning to take place.

The aqueous phases were extracted three times with chloroform (1:1.5 v/v). The chloroform layers were combined and evaporated. The residues obtained were resuspended in 100 μl of methanol and stored at −80° C. until they were used.

1 g of homogenate of each bivalve (Queen scallops, oysters, mussels and scallops) was subjected to the same treatment in order to serve as control.

Plate Preparation:

Serial dilutions of standard toxins, i.e. of 13-desmethyl spirolide C ($1.7\times10^{-5}$-$3.5\times10^{-12}$ M), 13,19-didesmethyl spirolide C ($3.3\times10^{-7}$-$2.1\times10^{-12}$ M) and gymnodimine A ($1.7\times10^{-5}$-$3.1\times10^{-11}$ M) (350 μl) were prepared with blocking buffer (TBS, 0.5% BSA). In the same way, each seafood extract, control or doped with said toxins, was diluted 100-fold and 200-fold (350 μl) in blocking buffer (TBS, 0.5% BSA). Each dose was analyzed in triplicate (100 μl per well).

13-Desmethyl spirolide C, 13,19-didesmethyl spirolide C and gymnodimine A are distributed commercially in methanol. The methanol concentrations were kept to a level below 1% in order to avoid any interference with the method.

Preparation of the Cyanobacterial Extracts

The crude extracts of cyanobacteria producing anatoxin-a were prepared as follows:

The biological material, i.e. cyanobacterial filaments, were harvested by centrifugation (3000 revolutions per minute at 15° C. for 10 minutes) from a culture of cyanobacteria. The cyanobacterial pellet was resuspended in distilled water and recentrifuged under the same conditions and lyophilized. The lyophilized cells were resuspended in 50 mM of acetic acid (10 mg: 2 ml) and lyzed by sonification (5 cycles of 1 minute with gaps of 3 minutes in ice) with a Branson 250 sonicator. The homogenate obtained was stirred for 4 hours in the dark and then centrifuged at 10 000 revolutions per minute for 30 minutes at 15° C. The supernatant was collected and then passed through a filtration unit (pore size 0.45 μm) and stored at −20° C. until use.

FIG. 4 A shows, on the same microplate, the dose dependent inhibition of biotin-α-BgTx-nAChR binding by serial dilutions of 13-desmethyl spirolide C and by seafood extracts doped with the same toxin and control extracts.

FIG. 4 B shows the inhibition of the biotin-α-BgTx-nAChR binding by serial dilutions of gymnodimine A and seafood extracts doped with gymnodimine A, and also by control seafood extracts tested at two concentrations (diluted 100-fold and 200-fold).

Furthermore, FIG. 4 C shows the inhibition of the biotin-α-BgTx-nAChR binding by serial dilutions of 13,19-didesmethyl spirolide and seafood extracts doped with the same toxin, and also by control seafood extracts. At the same time, the effect of the extracts obtained from the neurotoxic cyanobacteria *Oscillatoria*, strain PCC 6506 (producing anatoxin-a) and strain PCC 10111 (producing homoanatoxin-a), on the biotin-α-BgTx-nAChR binding, are shown.

The absorption data ($OD_{492\ nm}$) were expressed as percentage inhibition using the following formula: % inhibition=100×[(100% signal−signal of the sample)/(100% signal−(100% inhibition−plate signal))] or with the following formula: % inhibition=[100×(100% signal−signal of the sample)/(100% signal−100% inhibition)]. An inhibition curve for each of the toxins tested was constructed from the inhibition data obtained (FIG. 3 B). The inhibition parameter $IC_{50}$ (inhibition 50: 50% of nAChRs are occupied by the toxin preventing biotin-α-BgTx-nAChR binding) was calculated. The limit of detection (LOD) and the limit of quantification (LOQ) of the method were also calculated (see table 1).

The results obtained demonstrate that the nonradioactive biotin-α-bungarotoxin displacement method is applicable for the detection and quantification of marine phycotoxins, namely, for example, 13-desmethyl spirolide C, 13,19-didesmethyl spirolide C and gymnodimine A from contaminated seafood samples (FIGS. 4 A, 4 B, 4 C and 4 D) and of freshwater cyanobacterial neurotoxins, namely of anatoxin-a or of homoanatoxin-a (table 1).

The sensitivity of the method depends on the affinity of the toxin for the receptor. As demonstrated in this example, the detection threshold of this nonradioactive method is very low, for example 54 picograms of 13,19-didesmethyl spirolide C, 69 picograms of 13-desmethyl spirolide C and 101 picograms of gymnodimine A.

Figure 2:
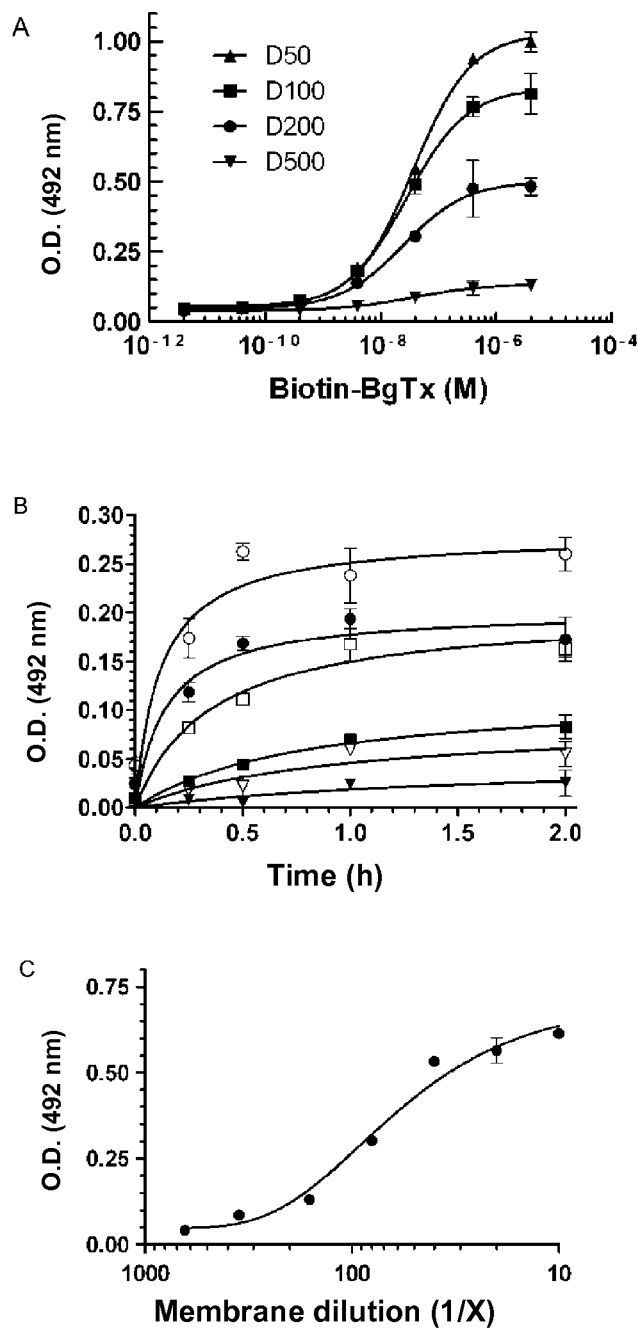
FIG. 2 represents standardization curves of the ligand-receptor binding displacement test on an ELISA microplate.

Furthermore, the method requires a very small amount of electrocyte membrane, for example from 1 to 2 μg of *Torpedo* electrocyte membrane proteins per well in this example (FIGS. 2 A, 2 B and 2 C). That is to say a very low consumption of *Torpedo* electrocyte membranes. In addition, when the *Torpedo* electrocyte membranes are appropriately stored, for example aliquots of 0.5 ml at −80° C., they are stable for several years.

Very important: microplates coated with *Torpedo* electrocyte membranes, when they are stored at 4° C. in 200 μl of blocking buffer (TBS, 0.5% BSA, pH 7.5), can be used for up to six months after manufacture thereof. There is no significant difference between plates coated the day before and plates coated six months beforehand for the detection of nAChR ligands. This proof of the principle is very useful for designing the manufacture of ready-to-use plates pre-coated with *Torpedo* electrocyte membranes.

The plates obtained in this example are denoted Torpecfo-MicroReceptor Plate.

As demonstrated in this example, the use of the device obtained by the method of the invention makes it possible to detect the interaction between nAChRs and competitive ligands directly on methanolic extracts of seafood and aqueous extracts of cyanobacterial filaments. In addition, the devices of the present invention, namely the ready-to-use plates pre-coated with *Torpedo* electrocyte membranes, could be transported and distributed by mail in order to be used in other countries/continents for the detection of competitive nAChR ligands.

Example 3: High-Throughput Screening of Nicotinic Acetylcholine Receptor Competitive Ligands/Toxins The microplates coated with *Torpedo* electrocyte membranes which are stored at 4° C., obtained in Example 1, are suitable for high-throughput methods.

A/ Use of the Liquidator 96™ 96-Tip Manual Pipetting Device (Rainin):

a) 96-Tube Plates to be Prepared Before Beginning the Detection Method:

A plate plan is prepared beforehand as represented in FIG. 5 B: seven extracts of environmental cyanobacteria tested in triplicate at three dilutions (10-, 100- and 1000-fold) and serial dilutions of 13,19-didesmethyl spirolide C ranging from $5 \times 10^{-7}$ to $5 \times 10^{-13}$ M, in addition to the negative controls (control plate, 3 wells), and 100% signal (6 wells) and 100% inhibition ($1 \times 10^{-5}$ M BgTx, 3 wells) controls, were tested using the method.

The plate of FIG. 6 C shows in rectangles the distribution of the seven marine cyanobacterial extracts and of the 13,19-didesmethyl spirolide C.

Rectangle I [A1-C3], CYA01; Rectangle II [D1-F3], CYA02; Rectangles III G1-G3 and [A4-B6], CYA03; Rectangle IV [C4-E6], CYA04; Rectangles V [F4-G6] and A7-A9, CYA 05; Rectangle VI [B7-D9], CYA06; Rectangle VII [E7-G9], CYA07; Rectangle VIII [A10-G12], 13,19-didesmethyl spirolide C.

According to the plate plan, solutions of toxin or of extract in blocking buffer identical to that of example mentioned are prepared and distributed in 96-tube plates capable of containing up to 1 ml of solution per tube: "TOXIN/EXTRACTS PLATE". For each standard toxin or sample to be tested in triplicate, the minimum volume to be prepared is 350 μl per tube.

A second 96-well plate containing a solution of $2.4 \times 10^{-7}$ M biotin-α-BgTx in blocking buffer (TBS, 0.5% BSA), "BIOTIN-α-BgTx PLATE", is prepared. The volume to be prepared depends on the number of plates to be tested (one 96-well microplate consumes 50 μl×96=4.8 ml). This solution is freshly prepared.

A third 96-tube plate, "PEROXIDASE PLATE", containing peroxidase-coupled streptavidin ($D_{5000}$ ~220 ng/nl protein in blocking buffer) is prepared. This solution is freshly prepared. The volume to be prepared depends on the number of plates to be tested (one 96-well microplate consumes 100 μl×96=9.6 ml).

A fourth 96-tube preparation plate indicated "OPD PLATE", containing the commercial substrate OPD, at least 120 μl per well, in order to produce a screening device, is prepared. This solution is freshly prepared and must be protected from light. The volume to be prepared depends on the number of plates to be tested (one 96-well microplate consumes 100 μl×96=9.6 ml). The OPD solution is prepared according to the supplier's protocol: 4 OPD tablets are dissolved in 12 ml of deionized water, to which 5 μl of hydrogen peroxide ($H_2O_2$) at 30% are added.

50 ml of stop solution for the peroxidase reaction (0.5 M $H_2SO_4$) are prepared in a rectangular dish suitable for the 96-channel manual pipetting device, denoted "STOP PLATE".

b) Procedure

The pre-coated screening device obtained according to the method described in Example 1, indicated *Torpedo*-MicroReceptor Plate hereinafter, is taken out of the refrigerator. The plate is left on a shaker at ambient temperature (25° C.) for 30 min. Once the screening device is at temperature, the adhesive film is removed, the blocking buffer is removed and, after having dried its surface, the plate is placed on the pipetting zone.

Incubations with Toxins/Extracts:

The 96-channel manual pipetting device is loaded with new tips and set to 100 μl, and the "TOXIN/EXTRACTS PLATE" is placed on a "loading" zone.

100 μl from the "TOXIN/EXTRACTS PLATE" containing toxin standards, samples, extracts, synthetic products or negative and positive controls, are sampled and introduced into the *Torpedo*-MicroReceptor Plate placed in the pipetting zone.

The screening device is sealed with an adhesive film (sealing tape, Costar) and left to incubate the immobilized *Torpedo* electrocyte membranes with the test samples for 3 h with shaking. Preferably, the incubation is carried out overnight at 4° C.

When the incubation is carried out at 4° C., the Torpecfo-MicroReceptor Plate is placed on a shaker at ambient temperature (25° C.) for 30 min before being placed again in the pipetting zone of the Liquidator 96™.

Incubation with the Biotin-α-BgTx Tracer

New tips are loaded, the pipetting device is set to 50 μl and the "BIOTIN-α-BgTx PLATE" is placed on the "loading" zone. 50 μl of each tube of the "BIOTIN-α-BgTx PLATE" are sampled and introduced directly into the Torpecfo-MicroReceptor Plate. The resulting plate corresponds to the screening device and is incubated for 30 min on a shaker at ambient temperature (25° C.), after which time the solution is removed and the plate is again placed in the pipetting zone.

Washing

New tips are loaded and 200 μl of washing solution (TBS, 0.1% Tween 20) are sampled and introduced into the *Torpedo*-MicroReceptor Plate wells. The washing solution is removed and the *Torpedo*-MicroReceptor Plate is again placed in the pipetting zone. This step is repeated three times.

Incubation with HRP-Streptavidin/Washing

100 μl of each tube of the "PEROXIDASE PLATE" are sampled and introduced directly into the screening device. The plate is incubated for 30 min on a shaker at ambient temperature (25° C.). The Torpecfo-MicroReceptor Plate is washed as previously described and is again placed in the pipetting zone.

Developing the Peroxidase Reaction and Stopping the Reaction

100 μl of each well of the "OPD PLATE" are sampled and introduced into the screening device. The *Torpedo*-MicroReceptor Plate is incubated until an optimum coloration is obtained, i.e. approximately 5 minutes, and 50 μl of the stop solution (0.5 M $H_2SO_4$) are introduced using the 96-tip pipetting device.

Reading and Analysis of Data

The Torpecfo-MicroReceptor Plate is read on the ELISA reader (GeniosPro, Tecan) and the results are analyzed.

The results are shown in FIG. 5. The plate, 100% signal and 100% nonspecific inhibition controls show that the analysis device is operating correctly and in a repetitive manner. In the seven extracts of environmental cyanobacteria of marine origin that were tested at three dilutions (10-fold: $D_{10}$: first row, 100-fold $D_{100}$: second row and 1000-fold: $D_{1000}$: third row), no nAChR ligands were detected. On the same plate, 13,19-didesmethyl spirolide C was tested: first row: $5\times10^{-7}$ M, second row $5\times10^{-8}$ M, third row: $5\times10^{-9}$ M, fourth row: $5\times10^{-10}$ M, fifth row: $5\times10^{-11}$ M, sixth row: $5\times10^{-12}$ M and seventh row: $5\times10^{-13}$ M. The inhibition of the biotin-α-BgTx-nAChR binding by 13,19-didesmethyl spirolide C is dose-dependent and confirms the results previously obtained for this toxin. The use of the 96-tip pipetting device accelerates the throughput of the analysis (10 microplates per day: 960 possible analyses). At the same time, the addition of the solutions containing either the toxins/extracts or the tracer, or the streptavidin-peroxidase, or the OPD substrate or the stop solution, simultaneously allows a more exact control of the reaction or incubation time.

B/ Use of an Automated Pipetting Device:

The following solutions: "TOXIN/EXTRACTS SOLUTION", "BIOTIN-α-BgTx SOLUTION", "PEROXIDASE SOLUTION", "OPD SOLUTION" and "STOP SOLUTION" are prepared as previously indicated.

A 96-well "model plate" is prepared for the samples of toxins/extracts/controls according to the test plate plan. The automated pipetting device is capable of automating the preparation of the toxin/sample dilutions, for the "model plate".

The steps are similar to the abovementioned steps.

Example 4: Method for Manufacturing Analysis Devices

The solutions, membranes and experimental conditions are identical to those of Example 2 mentioned above.

A dilution of the membrane stock solution, 2.7 mg of proteins per ml, prepared according to the method described in Examples 1-4 mentioned above, was diluted 200-fold in TBS buffer at a pH of 7.5.

100 μl of the 200-fold-diluted *Torpedo* membrane solution: 13.5 μg·ml$^{-1}$ total protein, i.e. 1.35 μg of membrane protein per well, were distributed into the wells of a Nunc Maxisorp (registered trade mark) flat-bottomed microplate, as represented in FIGS. 3, 4 and 5.

An adhesive film was placed over said plate and the plate was incubated at 4° C. overnight, i.e. 12-18 hours.

The excess membranes were removed by manually inverting the plate and the edges of the wells were cleaned with absorbent paper.

Finally, 200 μl of TBS blocking solution containing 0.5% BSA were introduced into each well. An adhesive film was placed over the plate termed Torpecfo-MicroReceptor Plate and stored at 4° C. until it was used.

The analysis device thus prepared is ready for use and in particular ready for transport.

Example 5: Comparison of the Known Detection Methods with the Method of the Invention In this example, the detection results obtained in the following prior art documents: Fonfria et al. [12], Vilarino et al. [13] and Arâoz et al. [14] were compared with those obtained with the method and device of the present invention (Examples 1 and 2 above).

Table 3 below represents the various results obtained, be they in terms of the sensitivity of the method according to the molecule to be detected.

TABLE 3 comparison of the method of the invention with the known methods

| | Fonfria et al. | Vilarino Natalia et al. | Arâoz et al. | Method of the invention |
|---|---|---|---|---|
| Sensitivity (concentration in nM) | 13,19-SPX C: 63.60 ± 3 | 13-SPX C: 108.2 ± 11.9<br>GYM A: 391.0 ± 55.3 | $ANTX_{CHEM}$: 62<br>$ANTX_{VISUAL}$: 17 | 13,19-SPX C: 3.10 (1.98-4.85)<br>13-SPX C: 6.84 (5.07-9.22)<br>GYM A: 74.23 (62.43-88.28)<br>ANTX: 68.81 (35.3-A34.2) |

TABLE 3-continued comparison of the method of the invention with the known methods

|  | Fonfria et al. | Vilarino Natalia et al. | Aráoz et al. | Method of the invention |
|---|---|---|---|---|
| Sensitivity (amount in µg of toxin in the well) |  | 13-SPX C: 85 |  | 13,19-SPX C: 0.051<br>13-SPX C: 0.069<br>GYM A: 0.101 |
| Limit of detection (nM) |  |  | $ANTX_{CHEM}$: 37<br>$ANTX_{VISUAL}$: 9 | 13,19-SPX C: 0.8<br>13-SPX C: 1<br>GYM A: 2<br>ANTX: 2 |
| Quantification range (nM) | 13,19-SPX C: 30-150 | 13-SPX C: 12.5-125.2<br>GYM A: 12.5-500 |  | 13,19-SPX C: 2-20<br>13-SPX C: 4-60<br>GYM A: 20-2000<br>ANTX: 30-2000 |
| Reading of data | Polarization fluorometer | Polarization fluorometer | Chemi-luminescence detector/visual | Microplate reader |
| Automation Transportable device (microplates) Stability of the device (microplates) |  |  |  | YES<br>YES (tested by rapid courier and by airplane)<br>6 months (tested) |

As demonstrated in this example, the use of the device obtained by means of the method of the invention makes it possible to detect the interaction between nAChRs and ligands with a much greater sensitivity than that of the prior art methods and devices.

In addition, the device of the present invention, namely the ready-to-use plates pre-coated with *Torpedo* electrocyte membranes, can be transported and distributed, for example by mail, for their use in other countries/continents for detecting competitive nAChR ligands.

Finally, as demonstrated in this example, the amounts of membrane fragments used for manufacturing the device of the invention are much smaller than the amounts required in the prior art methods. Thus, the method of the invention advantageously makes it possible to reduce the amount of membrane fragments to be used and thus reduces, compared with the prior art methods, the number of *Torpedoes* to be sacrificed while at the same time improving the sensitivity of detection of the device of the invention compared with the known devices/methods.

Example 6: Method for Eluting the Cyclized Imines having Reacted with the *Torpedo* Nicotinic Acetylcholine Receptors Immobilized on the Surface of the ELISA Plates Products Used:
The same products as in Example 1.
A ready-to-use analysis device obtained in Example 4 mentioned above, indicated Torpecfo-MicroReceptor Plate, i.e. a plate coated with *Torpedo* electrocyte membranes.
Gymnodimine A, 13-desmethyl spirolide C and 13,19-didesmethyl spirolide C standards.
Methanol.
2,5-Dihydroxybenzoic acid (DHB).
Acetonitrile.
Trifluoroacetic acid.

Equipment:
ELISA microplate reader
MALDI-TOF (Voyager-DE™ STR Workstation, Applied BioSystems, Foster City, Calif., USA)

Procedure:
The ready-to-use analysis device was placed at ambient temperature, namely 25° C., for 30 minutes.

The blocking buffer was removed and, without washing, six wells were incubated with 100 µl gymnodimine A, or 100 µl of 13-desmethyl spirolide C, or with 100 µl of 13,19-didesmethyl spirolide C, at a concentration of 1 µM, prepared in blocking buffer (TBS, 0.5% BSA, pH 7.5).

The device was incubated at 4° C. overnight.

After incubation of the device overnight at 4° C., the plate was placed at ambient temperature, namely 25° C., for 30 min, after which time the wells are washed 5 times with 250 µl of washing buffer comprising TBS, 0.1% Tween 20, pH 7.5.

The elution of the gymnodimine A was carried out with 50 µl of methanol added to each of the six wells previously incubated with this toxin. After 5 min of incubation at ambient temperature (25° C.), the methanol was recovered. The same procedure was applied for eluting 13-desmethyl spirolide C and 13,19-didesmethyl spirolide C.

The eluates were then analyzed by MALDI-TOF. For this, the matrix was prepared as follows: 10 mg of 2,5-dihydroxybenzoic acid were dissolved in 1 ml of a water-acetonitrile (1:1) mixture containing 0.3% (v/v) of trifluoroacetic acid.

For the analysis by MALDI-TOF, 10 µl of standard toxin (1 µM) were mixed with 10 µl of matrix prepared as previously described, using a vortex. One microliter of this mixture was deposited on the surface of a stainless steel sample plate (Perseptive Biosystems, Framingham, Mass., USA).

In the same way, 10 µl of each eluate were mixed with 10 µl of matrix prepared as previously described, using a vortex. One microliter of this mixture was deposited on the surface of a stainless steel sample plate. Once the solvent had evaporated off (namely 2 min after having deposited the samples), the sample plate was introduced into the MALDI-TOF instrument for the mass data acquisition.

TABLE 4

Physicochemical characterization of the eluates obtained from the wells in which the Torpedo nAChRs were incubated with cyclized imines

| Samples | MALDI-TOF | | UPLC/MS/MS ([M + H]⁺) |
|---|---|---|---|
| | Mass ([M + H]⁺) | Intensity (counts) | |
| Gymnodimine A (standard) | 508.35 | 22000 | 508.4 |
| Gymnodimine A (eluate from 6 wells) | 508.34 | 2000 | |
| 13-SPX C (10 µM standard) | 692.54 | 16000 | 692.4 |
| 13-SPX C (eluate from 6 wells) | 692.53 | 4906.4 | |
| 13,19-SPX C (10 µM standard) | 678.62 | 20000 | 678.4 |
| 13,19-SPX C (eluate from 6 wells) | 678.52 | 1800 | |

As demonstrated in this example, the use of the device obtained by means of the method of the invention makes it possible, for example, to capture cyclized imines which can then be eluted, for example with methanol. The use of the device obtained by means of the method of the invention therefore advantageously makes it possible to facilitate the isolation/characterization of nAChR ligands. In particular, it advantageously makes it possible to facilitate the isolation/physicochemical characterization of an nAChR agonist/antagonist, which is for example competitive. Thus, this device can also advantageously be used in programs for searching for new toxins.

REFERENCE LISTS

1. European parliament and counsel directive 2010/63/EU of Sep. 22, 2010, on the protection of animals used for scientific purposes. Official journal of the European Union. DOUEFR, Oct. 20, 2010 (http://eu.vlex.com/source/journal-officiel-union-europeenne-1 547/issue/2010/10/20/01).
2. Closure of the Conference on shellfish farming (Oct. 15, 2010). Speech by Bruno Le Maire, minister of food, agriculture and fisheries) (http://agriculture.gouv.fr/cloture-des-assises-de-la).
3. Fleming L E, Broad K, Clément A, Dewailly E, Elmir S, Knap A, Pomponi S A, Smith S, Gabriele H S, Walsh P (2006) Oceans and human health: Emerging public health risks in the marine environment. Mar. Pollut. Bull., 53: 545-560.
4. Molgô J, Girard E, Benoit E. (2007) Cyclic imines: an insight into this emerging group of bioactive marine toxins. In Phycotoxins: Chemistry and Biochemistry (Botana, L. M., ed) pp. 319-335, Blackwell Publishing Ltd, Iowa.
5. Amzil Z, Sibat M, Royer F, Masson N, Abadie E. (2007) Report on the first detection of pectenotoxin-2, spirolide-A and their derivatives in French shellfish. Mar. Drugs 5: 168-179.
6. Bourne Y, Radie Z, Araôz R, Talley T T, Benoit E, Servent D, Taylor P, Molgô J, Marchot P. (2010) Structural determinants in phycotoxins and AChBP conferring high affinity binding and nicotinic AChR antagonism. Proc. Natl. Acad. Sci. U.S.A. 107: 6076-6081.
7. Kharrat R, Servent D, Girard E, Ouanounou G, Amar M, Marrouchi R, Benoit E, Molgô J. (2008) The marine phytotoxin gymnodimine targets muscular and neuronal nicotinic acetylcholine receptor subtypes with high affinity. J. Neurochem. 107, 952-963.
8. Araôz R, Servent D, Molgô J, Iorga B I, Fruchart-Gaillard C, Benoit E, Gu Z, Stivala C, Zakarian A. (2011) Total synthesis of pinnatoxins A and G and revision of the mode of action of pinnatoxin A. J. Am. Chem. Soc. 133, 10499-10511.
9. Sivonen K, Jones G. (1999) Cyanobacterial toxins. In Toxic cyanobacteria in water: a guide to their public health consequences, monitoring and management (Chorus, I., ed) pp. 41-111, Bartram, J. E. & F. N. Spon, London.
10. Gugger M, Lenoir S, Berger C, Ledreux A, Druart J C, Humbert J F, Guette C, Bernard C. (2005) First report in a river in France of the benthic cyanobacterium Phormidium favosum producing anatoxin-a associated with dog neurotoxicosis. Toxicon 45, 919-928.
11. Cadel-Six S. Peyraud-Thomas C, Brient L, Tandeau de Marsac N, Rippka R, Mejean A. (2007) Different genotypes of anatoxin-producing cyanobacteria coexist in the Tarn River, France. Applied and Environmental Microbiology 73, 7605-7614.
12. Fonfria E S, Vilarino N, Molgô J, Araôz R, Otero P, Espiha B, Louzao M C, Alvarez M, Botana L M (2010) Detection of 13,19-didesmethyl C spirolide by fluorescence polarization using Torpedo electrocyte membranes. Anal. Biochem. 403: 102-107.
13. Vilarino N, Fonfria E S, Molgô J, Araôz R, Botana L M (2009). Detection of Gymnodimine-A and 13-Desmethyl C Spirolide Phycotoxins by Fluorescence Polarization. Analytical Chemistry, 81: 2708-2714.
14. Araôz R, Herdman M, Rippka R, Ledreux A, Molgô J, Changeux J P, Tandeau de Marsac N, Nghiêm H O. (2008). A non-radioactive ligand-binding assay for detection of cyanobacterial anatoxins using Torpedo electrocyte membranes. Toxicon 52:163-174.
15. Morel N, Marsal J, Manaranche R, Lazereg S, Mazie J C, Israël M (1985). Large-scale purification of presynaptic plasma membranes from Torpedo marmorata electric organ. J. Cell Biol., 10: 1757-1762.
16. Hill J A, Nghiêm H-O & Changeux J-P (1991). Serine-specific phosphorylation of nicotinic receptor associated 43K protein. Biochemistry, 30, 5579-5585.
17. Changeux J P (2010). Allosteric receptors: from electric organ to cognition. Annu Rev Pharmacol Toxicol, 50, 1-38.
18. Esser P (2010). Principles in Adsorption to Polystyrene. Technical Bulletin: 06a. Thermo Fisher Scientific Inc.
19. Araôz R, Molgô J, Tandeau de Marsac N T (2009) Neurotoxic cyanobacterial toxins. Toxicon 56: 813-828.
20. Da Costa C J B, Kaiser D E E, Baenziger J E (2005). Role of Glycosylation and Membrane Environment in Nicotinic Acetylcholine Receptor Stability. Biophys J, 88, 1755-1764.

The invention claimed is:
1. A method for manufacturing an analysis device for detection, quantification, and physicochemical identification of neurotoxins, the analysis device comprising Torpedo membrane fragments immobilized at the surface thereof, the method comprising the steps of:
 a. isolating Torpedo electrocyte cell membranes,
 b. fragmenting said isolated membranes, c. incorporating the membrane fragments obtained in step b into a solution with a pH from 6.5 to 10 and ionic strength from 0.1 mol/L to 0.7 mol/L, d. attaching said membrane fragments to the surface of the device by non-covalent and non-ionic interaction between the membrane fragments and the surface, wherein the surface of the device is made of plastic, and wherein the membrane fragments are not chemically modified before attaching to the surface.

2. The method according to claim 1, wherein the method comprises, before the step d of immobilizing the membrane fragments on the device, a step c' of diluting the membrane fragments.

3. The method according to claim 1, wherein the total protein concentration in said solution with a pH from 6.5 to 10 is from 5 to 200 µg/ml.

4. The method according to claim 1, wherein the *Torpedo* is *Torpedo marmorata* or *Torpedo californica*.

5. The method according to claim 1, wherein the membranes are plasma membranes of electrocyte cells.

6. The method according to claim 1, wherein the surface is a microplate and/or strip well surface.

7. The method according to claim 1, wherein the membrane fragments are attached to the surface via non-covalent interactions and formation of hydrogen bridges between the membrane fragments and the surface.

8. The method according to claim 1, wherein the device is a 96- or 384-well ELISA plate, or a 4-, 8- or 12-well plate, or 6-, 8- or 12-well strips, and the amount of protein in the membrane fragments attached to the surface of the device is 0.5 to 5 µg of protein per well.

9. The method according to claim 8, wherein the amount of protein is 1 to 2 µg of protein per well.

10. The method according to claim 8, wherein the amount of protein is 1 to 1.5 µg of protein per well.

11. The method according to claim 1, wherein the solution is selected from the group consisting of (a) a tris buffered saline (TBS) solution consisting of 150 mM NaCl and 50 mM Tris having pH of 7.5, (b) a phosphate buffered saline (PBS) S) comprising 130 mM sodium chloride, 10 mM sodium phosphate, having pH of 7.0, and (c) a carbonate/bicarbonate buffer comprising 150 mM sodium chloride, 100 mM sodium carbonate, having a pH of 9.5.

12. An analysis device obtained by the method according to claim 1, wherein the surface of the device is made of plastic.

13. The device according to claim 12, wherein the membrane fragments are attached to the surface of wells.

14. The device according to claim 12, wherein the device is a 96- or 384-well ELISA plate, or a 4-, 8- or 12-well plate, or 6-, 8- or 12-well strips.

15. The device according to claim 14, wherein the amount of protein in the membrane fragments attached to the surface of the device is 0.5 to 5 µg of protein per well.

16. The device according to claim 12, wherein the device is configured for detecting and quantifying neurotoxins.

17. The device according to claim 16, wherein the neurotoxins act on nicotinic acetylcholine receptors.

18. The device according to claim 12, wherein the device is configured for detecting and quantifying nicotinic acetylcholine receptor ligands.

19. The device according to claim 12, wherein the device is configured for the high-throughput screening of nicotinic acetylcholine receptor ligands.

20. The device according to claim 12, wherein the device is configured for the purification and physicochemical characterization of nicotinic acetylcholine receptor ligands.

21. A method for manufacturing an analysis device for detection, quantification, and physicochemical identification of neurotoxins, the analysis device comprising *Torpedo* membrane fragments immobilized at the surface thereof, the method comprising the steps of:

a. isolating *Torpedo* electrocyte cell membranes, b. fragmenting said isolated membranes, c. incorporating the membrane fragments obtained in step b into a solution with a pH from 6.5 to 10 and ionic strength from 0.1 mol/L to 0.7 mol/L, d. attaching said membrane fragments to the surface of the device by non-covalent and non-ionic interaction between the membrane fragments and the surface, e. capturing the neurotoxins contained in a sample by incubating the sample with the analysis device;

f washing the analysis device with a washing buffer;

g. recovering the captured neurotoxins by eluting them with an eluting solution, wherein the surface of the device is made of plastic, and wherein the membrane fragments are not chemically modified before attaching to the surface.

22. The method of claim 21, wherein the method further comprises the step:

h. analyzing the eluted neurotoxins by mass spectrometry.

23. The method of claim 21, wherein the washing buffer is a Tris buffered saline (TBS) containing 0.1% Tween 20.

24. The method of claim 21, wherein the eluting solution comprises methanol.

* * * * *

UNITED STATES PATENT AND TRADEMARK OFFICE
CERTIFICATE OF CORRECTION

PATENT NO. : 10,073,089 B2
APPLICATION NO. : 13/981859
DATED : September 11, 2018
INVENTOR(S) : Romulo Araoz et al.

Page 1 of 1

It is certified that error appears in the above-identified patent and that said Letters Patent is hereby corrected as shown below:

On the Title Page

Item (73) Assignee, delete "ABRAXIS LLC , Warminster , PA (US)" and insert -- CENTRE NATIONAL DE LA RECHERCHE SCIENTIFIQUE-CNRS, Paris-Cedex (FR); INSTITUT PASTEUR, Paris (FR); UNIVERSIDAD DE COMPOSTELA, Santiago de Compostela (ES) --, therefor.

Signed and Sealed this
Fifth Day of May, 2020

Andrei Iancu
*Director of the United States Patent and Trademark Office*